(12) United States Patent
Fischer et al.

(10) Patent No.: US 8,314,254 B2
(45) Date of Patent: Nov. 20, 2012

(54) SUBSTITUTED SPIROCYCLIC KETOENOLS

(75) Inventors: Reiner Fischer, Monheim (DE); Thomas Bretschneider, Lohmar (DE); Christoph Erdelen, Leichlingen (DE); Angelika Lubos-Erdelen, legal representative, Leichlingen (DE); Jorg Konze, Cologne (DE); Peter Losel, Leverkusen (DE); Mark Wilhelm Drewes, Langenfeld (DE); Dieter Feucht, Eschborn (DE); Karl-Heinz Kuck, Langenfeld (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 93 days.

(21) Appl. No.: 12/786,765

(22) Filed: May 25, 2010

(65) Prior Publication Data
US 2010/0234229 A1  Sep. 16, 2010

Related U.S. Application Data

(63) Continuation of application No. 10/525,920, filed as application No. PCT/EP03/09103 on Aug. 18, 2003, now Pat. No. 7,754,654.

(30) Foreign Application Priority Data

Aug. 28, 2002  (DE) .................................. 10239479

(51) Int. Cl.
C07D 209/00 (2006.01)
C07D 209/54 (2006.01)
A01N 43/48 (2006.01)
A01N 43/52 (2006.01)

(52) U.S. Cl. ......... 548/408; 504/282; 504/283; 504/315
(58) Field of Classification Search .................. 548/408; 504/282, 283, 294, 315
See application file for complete search history.

(56) References Cited

U.S. PATENT DOCUMENTS

| | | | |
|---|---|---|---|
| 5,258,527 A | 11/1993 | Krauskopf et al. |
| 5,262,383 A | 11/1993 | Fischer et al. |
| 5,462,913 A | 10/1995 | Fischer et al. |
| 5,504,057 A | 4/1996 | Fischer et al. |
| 5,567,671 A | 10/1996 | Fischer et al. |
| 5,589,469 A | 12/1996 | Fischer et al. |
| 5,602,078 A | 2/1997 | Fischer et al. |
| 5,610,122 A | 3/1997 | Fischer et al. |
| 5,616,536 A | 4/1997 | Fischer et al. |
| 5,622,917 A | 4/1997 | Fischer et al. |
| 5,677,449 A | 10/1997 | Fischer et al. |
| 5,719,310 A | 2/1998 | Fischer et al. |
| 5,830,825 A | 11/1998 | Fischer et al. |
| 5,830,826 A | 11/1998 | Fischer et al. |
| 5,847,211 A | 12/1998 | Fischer et al. |
| 5,981,567 A | 11/1999 | Fischer et al. |
| 5,994,274 A | 11/1999 | Fischer et al. |
| 6,051,723 A | 4/2000 | Fischer et al. |
| 6,110,872 A | 8/2000 | Lieb et al. |
| 6,114,374 A | 9/2000 | Lieb et al. |
| 6,172,255 B1 | 1/2001 | Fischer et al. |
| 6,200,932 B1 | 3/2001 | Fischer et al. |
| 6,251,830 B1 | 6/2001 | Fischer et al. |
| 6,255,342 B1 | 7/2001 | Lieb et al. |
| 6,288,102 B1 | 9/2001 | Hagemann et al. |
| 6,316,486 B1 | 11/2001 | Lieb et al. |
| 6,359,151 B2 | 3/2002 | Lieb et al. |
| 6,380,246 B1 | 4/2002 | Lieb et al. |
| 6,391,912 B1 | 5/2002 | Hagemann et al. |
| 6,451,843 B1 | 9/2002 | Lieb et al. |
| 6,458,965 B1 | 10/2002 | Lieb et al. |
| 6,469,196 B2 | 10/2002 | Fischer et al. |
| 6,472,419 B1 | 10/2002 | Fischer et al. |
| 6,479,489 B1 | 11/2002 | Fischer et al. |
| 6,504,036 B1 | 1/2003 | Lieb et al. |
| 6,511,942 B1 | 1/2003 | Lieb et al. |
| 6,555,567 B1 | 4/2003 | Fischer et al. |
| 6,596,873 B1 | 7/2003 | Lieb et al. |
| 6,608,211 B1 | 8/2003 | Hagemann et al. |
| 6,630,594 B2 | 10/2003 | Hagemann et al. |
| 6,670,488 B1 | 12/2003 | Hagemann et al. |
| 6,693,092 B2 | 2/2004 | Lieb et al. |

(Continued)

FOREIGN PATENT DOCUMENTS

EP  596298  10/1993

(Continued)

OTHER PUBLICATIONS

Dorwald, F. A., Side Reactions in Organic Synthesis, 2005, Wiley: VCH, Weinheim pg. IX of Preface.*

Norman O.V. Sonntag, "The Reactions of Aliphatic Acid Chlorides", Chemical Reviews, 52, (month unavailable) 1953, pp. 237-416.

Bhabatosh Bhattacharya, "Isoquinoline Derivatives: Part XVIII—Formation of I-Alkyl-(or alkaryl or aryl)-3-methyl-7-chloro-(or 5-chloro)-isoquinolines", Indian J. Chem., vol. 6, Jul. 1968, pp. 341-345.

(Continued)

Primary Examiner — Sabiha Qazi
(74) Attorney, Agent, or Firm — Baker Donelson Bearman Caldwell & Berkowitz, PC

(57) ABSTRACT

The present invention relates to novel intermediates used in the preparation of substituted spirocyclic ketoenols of the formula (I)

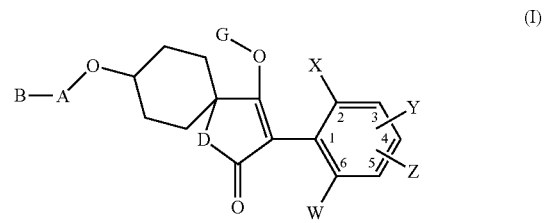

in which W, X, Y, Z, A, B, D and G are as defined in the disclosure.

4 Claims, No Drawings

U.S. PATENT DOCUMENTS

| | | |
|---|---|---|
| 6,759,548 B2 | 7/2004 | Fischer et al. |
| 6,774,133 B2 | 8/2004 | Fischer et al. |
| 6,806,264 B2 | 10/2004 | Lieb et al. |
| 7,754,654 B2 * | 7/2010 | Fischer et al. ............ 504/282 |
| 2002/0010204 A1 | 1/2002 | Lieb et al. |
| 2002/0022575 A1 | 2/2002 | Fischer et al. |
| 2002/0161034 A1 | 10/2002 | Hagemann et al. |
| 2003/0073851 A1 | 4/2003 | Lieb et al. |
| 2003/0096806 A1 | 5/2003 | Lieb et al. |
| 2003/0144504 A1 | 7/2003 | Fischer et al. |
| 2003/0171219 A1 | 9/2003 | Lieb et al. |
| 2003/0199572 A1 | 10/2003 | Lieb et al. |
| 2003/0216260 A1 | 11/2003 | Ruther et al. |
| 2003/0228984 A1 | 12/2003 | Hagemann et al. |
| 2004/0019061 A1 | 1/2004 | Fischer et al. |
| 2004/0102327 A1 | 5/2004 | Hagemann et al. |
| 2004/0127365 A1 | 7/2004 | Lieb et al. |

FOREIGN PATENT DOCUMENTS

| | | |
|---|---|---|
| EP | 2382435 | 3/2001 |
| EP | 2384501 | 4/2001 |
| JP | 2002-205984 | 7/2002 |
| WO | 96/25395 | 8/1996 |
| WO | 97/17092 | 5/1997 |
| WO | 97/36868 | 10/1997 |
| WO | 98/25638 | 6/1998 |
| WO | 99/16748 | 4/1999 |
| WO | 99/43649 | 9/1999 |
| WO | 00/68196 | 11/2000 |
| WO | 02/02523 | 1/2002 |

OTHER PUBLICATIONS

H.R. Harrison et al., "Use of molecular sieves in the methyl esterification of carboxylic acids", Chem. Ind. (London), Nov. 9, 1968, p. 1568.

P.L. Compagnon Et M. Miocque, "Addition Des Reactifs Nucleophiles Sur La Triple Liaison Nitrile", Ann. Chim, 14, 5, (month unavailable) 1970, pp. 23-38.

L. Munday, "Amino-acids of the Cyclohexane Series", J. Chem. Soc. (month unavailable) 1961, pp. 4372-4379.

John T. Edward et al., Sterochemisktry of the Bucherer-Bergs, and Strecker Reactions of 4-tert-Butylcyclohexanone, Can J. Chem., 53, (month unavailable) 1975, pp. 3339-3350.

* cited by examiner

SUBSTITUTED SPIROCYCLIC KETOENOLS

This application is a continuation of U.S. application Ser. No. 10/525,920, filed Feb. 25, 2005, which was filed under 35 U.S.C. 371 as a national stage application of PCT/EP2003/009103, filed Aug. 18, 2003, which was published in German as International Patent Publication WO 2004/024688 on Mar. 25, 2004, and is entitled to the right of priority of German Patent Application 102 39 479.2, filed Aug. 28, 2002.

The present invention relates to novel substituted spirocyclic ketoenols, to a plurality of processes for their preparation and to their use as pesticides, microbicides and herbicides.

1H-Arylpyrrolidinediene derivatives having herbicidal, insecticidal or acaricidal action are known: EP-A-456 063, EP-A-521 334, EP-A-613 884, EP-A-613 885, WO 95/01 358, WO 98/06 721, WO 98/25 928, WO 99/16 748, WO 99/24 437 or WO 01/17 972.

Also known are alkoxy-substituted spirocyclic 1H-arylpyrrolidinedione derivatives: EP-A-596 298, WO 95/26 954, WO 95/20 572, EP-A-0 668 267, WO 96/25 395, WO 96/35 664, WO 97/01 535, WO 97/02 243, WO 97/36 868, WO 98/05 638, WO 99/43 649, WO 99/48 869, WO 99/55 673, WO 01/23 354, WO 01/74 770, WO 01/17 972.

It is known that certain $\Delta^3$-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972.

However, the herbicidal and/or acaricidal and/or insecticidal activity and/or the activity spectrum and/or the compatibility of the known compounds with plants, in particular with crop plants, is not always satisfactory.

This invention now provides novel compounds of the formula (I)

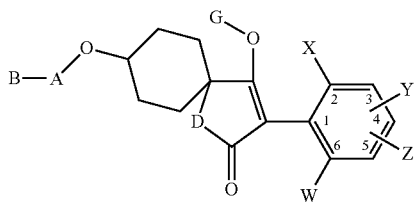

(I)

in which
W represents alkyl or alkoxy,
X represents halogen, alkyl, alkoxy, haloalkyl, haloalkoxy or cyano,
Y in the 4-position represents hydrogen, halogen, cyano or haloalkyl,
Z represents hydrogen,
W also represents hydrogen, halogen or alkyl,
X also represents halogen, alkyl, alkoxy, haloalkyl, haloalkoxy or cyano,
Y in the 4-position also represents optionally substituted phenyl,
Z also represents hydrogen,
W likewise represents hydrogen or alkyl,
X likewise represents halogen, alkyl, alkoxy, haloalkyl, haloalkoxy or cyano,
Y in the 5-position likewise represents optionally substituted phenyl,
Z in the 4-position likewise represents hydrogen, alkyl or halogen,
W moreover represents hydrogen, methyl, propyl, isopropyl or halogen,
X moreover represents halogen, alkyl, alkoxy, haloalkyl, haloalkoxy or cyano,
Y in the 3- or 5-position moreover represents hydrogen, halogen or alkyl,
Z in the 4-position moreover represents hydrogen, halogen, alkyl, haloalkyl, cyano or haloalkoxy,
A represents an optionally substituted alkanediyl group or represents cycloalkyl which is optionally substituted and/or optionally interrupted by a heteroatom,
B represents optionally substituted alkenyl, alkoxy, alkoxyalkyloxy, phenyl, hetaryl or represents cycloalkyl which is optionally substituted and/or optionally interrupted by heteroatoms and/or C=O,
D represents NH or oxygen,
G represents hydrogen (a) or represents one of the groups

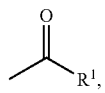

(b)

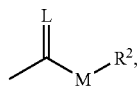

(c)

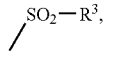

(d)

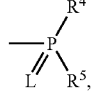

(e)

E, or (f)

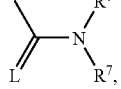

(g)

where
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl,
$R^2$ represents in each case optionally halogen- or cyano-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio,
$R^6$ and $R^7$ independently of one another represent hydrogen, represent in each case optionally halogen- or cyano-substituted alkyl, cycloalkyl, alkenyl, alkoxy, alkoxyalkyl, represents in each case optionally substituted phenyl or benzyl, or together with the N atom to which they are attached form a cycle which optionally contains oxygen or sulphur and which is optionally substituted.

Depending inter alia on the nature of the substituents, the compounds of the formula (I) can be present as optical isomers or isomer mixtures of varying composition which, if appropriate, can be separated in a customary manner. The present invention provides both the pure isomers and the isomer mixtures, their preparation and use as well as compositions comprising them. However, hereinbelow for the sake of simplicity only compounds of the formula (I) are referred to although this means both the pure compounds and, if appropriate, also mixtures having varying proportions of isomeric compounds.

Including D being NH (1) and D being O (2), the following principal structures (I-1) and (I-2) result:

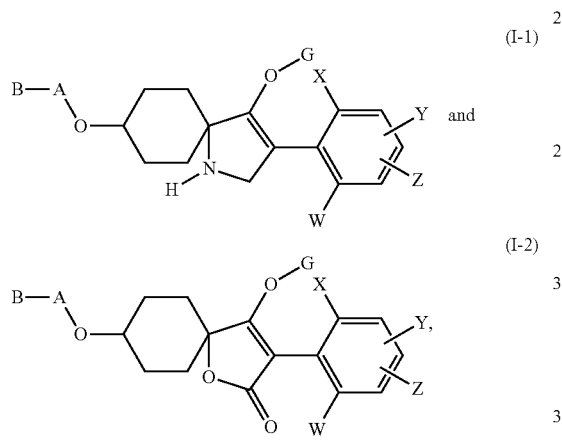

in which
A, B, G, W, X, Y and Z are as defined above.

Including the different meanings (a), (b), (c), (d), (e), (f) and (g) of the group G, the following principal structures (I-1-a) to (I-1-g) result if D represents NH (1),

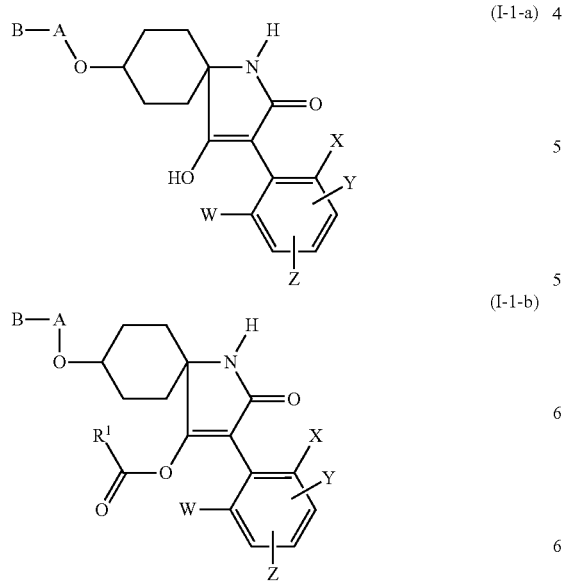

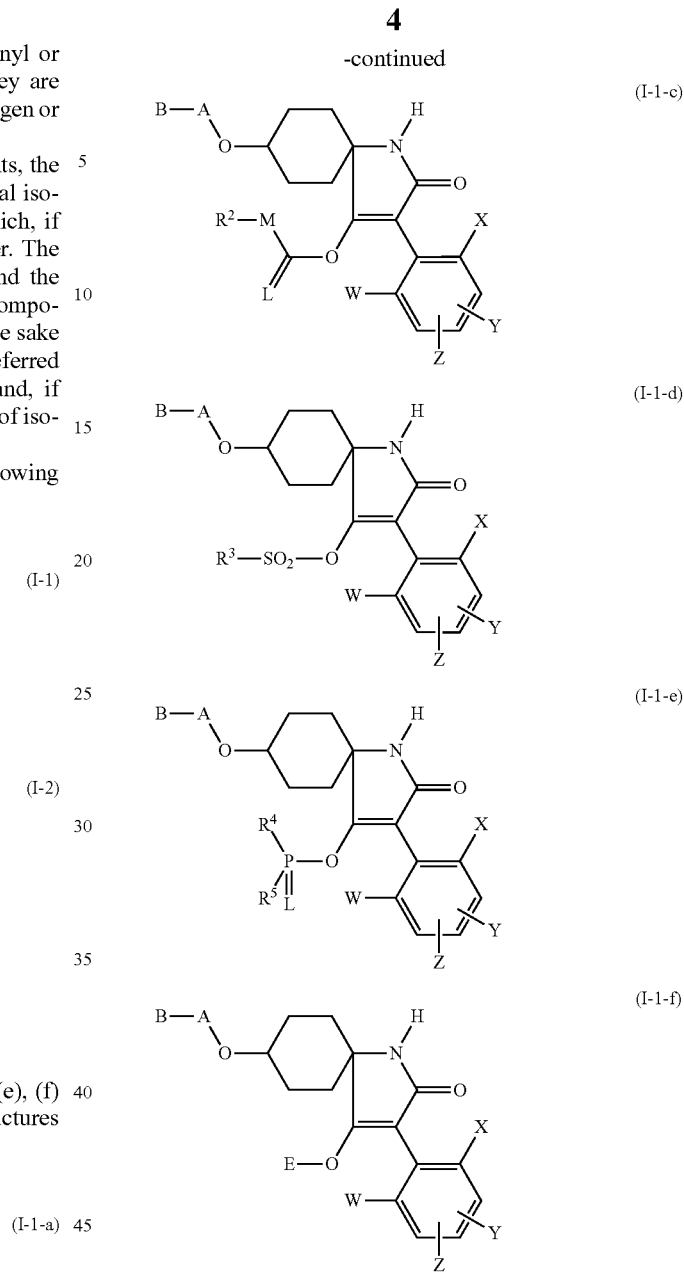

in which
A, B, E, L, M, W, X, Y, Z, $R^1$, $R^2$, $R^3$, $R^4$, $R^5$, $R^6$ and $R^7$ are as defined above.

Including the different meanings (a), (b), (c), (d), (e), (f) and (g) of the group G, the following principal structures (I-2-a) to (I-2-g) result if D represents O (2),

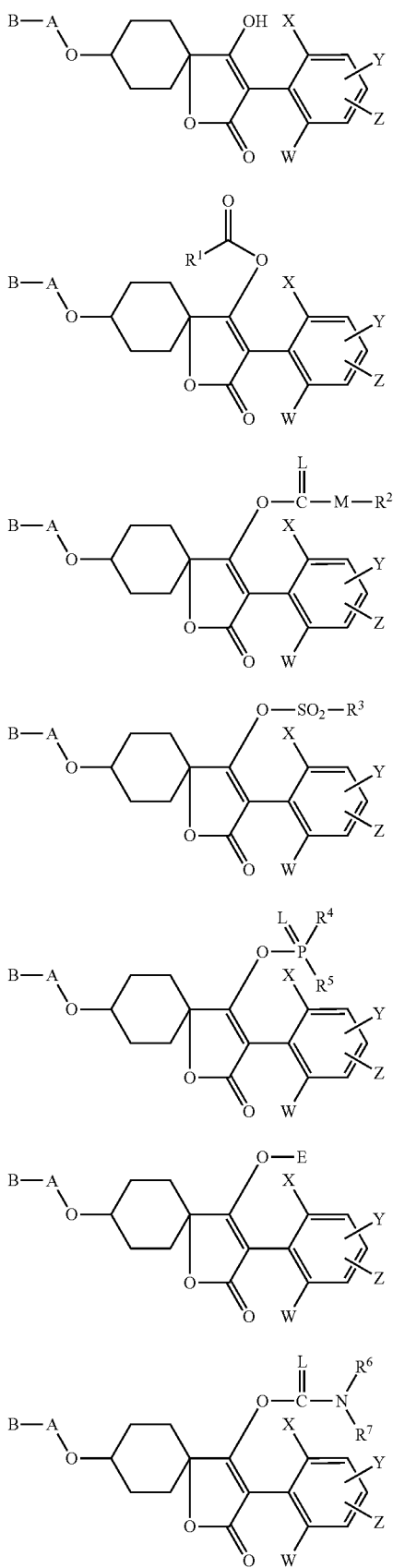

in which
A, B, E, L, M, W, X, Y, Z, R¹, R², R³, R⁴, R⁵, R⁶ and R⁷ are as defined above.

Furthermore, it has been found that the novel compounds of the formula (I) are obtained by the processes described below:

(A) compounds of the formula (I-1-a),

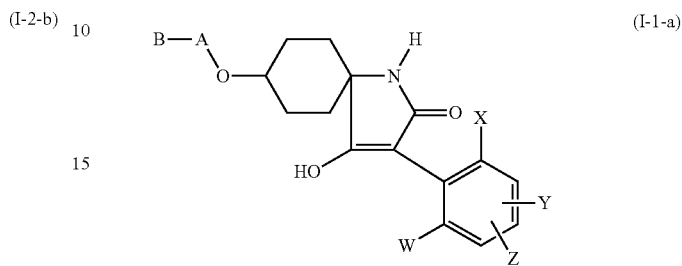

in which
A, B, W, X, Y and Z are as defined above, are obtained when
compounds of the formula (II),

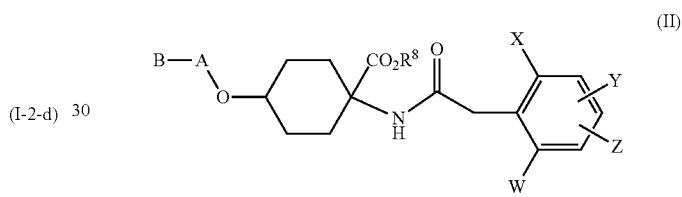

in which
A, B, W, X, Y and Z are as defined above
and
R⁸ represents alkyl (preferably $C_1$-$C_6$-alkyl),
are condensed intramolecularly in the presence of a diluent and in the presence of a base.

(B) Moreover, it has been found that compounds of the formula (I-2-a),

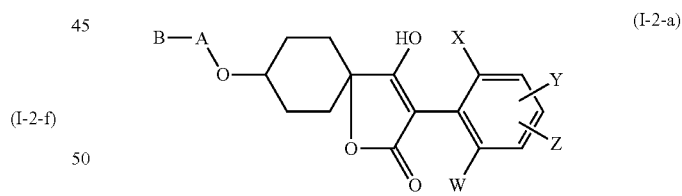

in which
A, B, W, X, Y and Z are as defined above
are obtained when
compounds of the formula (III),

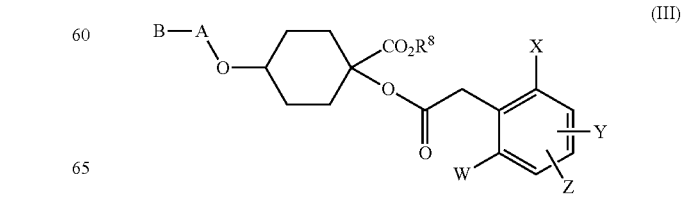

in which

A, B, W, X, Y, Z and $R^8$ are as defined above are condensed intramolecularly in the presence of a diluent and in the presence of a base.

Moreover, it has been found (C) that the compounds of the formulae (I-1-b) to (I-2-b) shown above in which $R^1$, A, B, W, X, Y and Z are as defined above are obtained when compounds of the formulae (I-1-a) to (I-2-a) shown above in which A, B, W, X, Y and Z are as defined above are in each case α) reacted with compounds of the formula (IV)

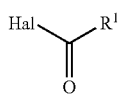
(IV)

in which $R^1$ is as defined above and

Hal represents halogen (in particular chlorine or bromine)

or

β) are reacted with carboxylic anhydrides of the formula (V), $$R^1-CO-O-CO-R^1 \quad (V)$$

in which $R^1$ is as defined above, if appropriate in the presence of a diluent and if appropriate in the presence of an acid binder;

(D) that the compounds of the formulae (I-1-c) to (I-2-c) shown above in which $R^2$, A, B, W, M, X, Y and Z are as defined above and L represents oxygen are obtained when compounds of the formulae (I-1-a) to (I-2-a) shown above in which A, B, W, X, Y and Z are as defined above are in each case reacted with chloroformic esters or chloroformic thioesters of the formula (VI), $$R^2\text{-M-CO-Cl} \quad (VI)$$

in which $R^2$ and M are as defined above, if appropriate in the presence of a diluent and if appropriate in the presence of an acid binder;

(E) that compounds of the formulae (I-1-c) to (I-2-c) shown above in which $R^2$, A, B, W, M, X, Y and Z are as defined above and L represents sulphur are obtained when compounds of the formulae (I-1-a) to (I-2-a) shown above in which A, B, W, X, Y and Z are as defined above are in each case reacted with chloromonothioformic esters or chlorodithioformic esters of the formula (VII),

(VII)

in which

M and $R^2$ are as defined above, if appropriate in the presence of a diluent and if appropriate in the presence of an acid binder;

(F) that compounds of the formulae (I-1-d) to (I-2-d) shown above in which $R^3$, A, B, W, X, Y and Z are as defined above are obtained when compounds of the formulae (I-1-a) to (I-2-a) shown above in which A, B, W, X, Y and Z are as defined above are in each case reacted with sulphonyl chlorides of the formula (VIII), $$R^3-SO_2-Cl \quad (VIII)$$

in which $R^3$ is as defined above, if appropriate in the presence of a diluent and if appropriate in the presence of an acid binder;

(G) that compounds of the formulae (I-1-e) to (I-2-e) shown above in which L, $R^4$, $R^5$, A, B, W, X, Y and Z are as defined above are obtained when compounds of the formulae (I-1-a) to (I-2-a) shown above in which A, B, W, X, Y and Z are as defined above are in each case reacted with phosphorus compounds of the formula (IX),

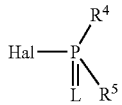
(IX)

in which

L, $R^4$ and $R^5$ are as defined above and

Hal represents halogen (in particular chlorine or bromine), if appropriate in the presence of a diluent and if appropriate in the presence of an acid binder, (H) that compounds of the formulae (I-1-f) to (I-2-0 shown above in which E, A, B, W, X, Y and Z are as defined above are obtained when compounds of the formulae (I-1-a) to (I-2-a) in which A, B, W, X, Y and Z are as defined above are in each case reacted with metal compounds or amines of the formulae (X) and (XI), respectively, $$Me(OR^{10})_t \quad (X)$$

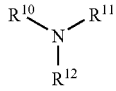
(XI)

in which

Me represents a mono- or divalent metal (preferably an alkali metal or an alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (I) that compounds of the formulae (I-1-g) to (I-2-g) shown above in which L, $R^6$, $R^7$, A, B, W, X, Y and Z are as defined above are obtained when compounds of the formulae (I-1-a) to (I-2-a) shown above in which A, B, W, X, Y and Z are as defined above are in each case α) reacted with isocyanates or isothiocyanates of the formula (XII), $$R^6-N=C=L \quad (XII)$$

in which $R^6$ and L are as defined above, if appropriate in the presence of a diluent and if appropriate in the presence of a catalyst, or β) are reacted with carbamoyl chlorides or thiocarbamoyl chlorides of the formula (XIII),

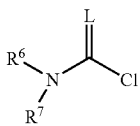

(XIII)

in which

L, $R^6$ and $R^7$ are as defined above, if appropriate in the presence of a diluent and if appropriate in the presence of an acid binder.

Furthermore, it has been found that the novel compounds of the formula (I) are highly active pesticides, preferably insecticides, acaricides and/or fungicides and/or herbicides, and are additionally frequently tolerated very well by plants, in particular by crop plants.

The formula (I) provides a general definition of the compounds according to the invention. Preferred substituents or ranges of the radicals listed in the formulae mentioned above and below are illustrated below:

W preferably represents $C_1$-$C_6$-alkyl or $C_1$-$C_6$-alkoxy,

X preferably represents halogen, $C_1$-$C_6$-alkyl, $C_1$-$C_6$-alkoxy, $C_1$-$C_4$-haloalkyl, $C_1$-$C_4$-haloalkoxy or cyano, Y in the 4-position preferably represents hydrogen, halogen, cyano or $C_1$-$C_4$-haloalkyl, Z preferably represents hydrogen, W also preferably represents hydrogen, halogen or $C_1$-$C_6$-alkyl, X also preferably represents halogen, $C_1$-$C_6$-alkyl, $C_1$-$C_6$-alkoxy, $C_1$-$C_4$-haloalkyl, $C_1$-$C_4$-haloalkoxy or cyano, Y in the 4-position also preferably represents the radical

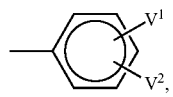

Z also preferably represents hydrogen, $V^1$ also preferably represents halogen, $C_1$-$C_{12}$-alkyl, $C_1$-$C_6$-alkoxy, $C_1$-$C_4$-haloalkyl or $C_1$-$C_4$-haloalkoxy, $V^2$ also preferably represents hydrogen, halogen, $C_1$-$C_6$-alkyl, $C_1$-$C_6$-alkoxy or $C_1$-$C_4$-haloalkyl, $V^1$ and $V^2$ together also preferably represent $C_3$-$C_4$-alkanediyl which may optionally be substituted by halogen and/or $C_1$-$C_2$-alkyl and which may optionally be interrupted by one or two oxygen atoms, W likewise preferably represents hydrogen or $C_1$-$C_6$-alkyl, X likewise preferably represents halogen, $C_1$-$C_6$-alkyl, $C_1$-$C_6$-alkoxy, $C_1$-$C_4$-haloalkyl, $C_1$-$C_4$-haloalkoxy or cyano, Y in the 5-position likewise preferably represents the radical

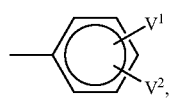

Z in the 4-position likewise preferably represents hydrogen, $C_1$-$C_6$-alkyl or halogen, $V^1$ likewise preferably represents halogen, $C_1$-$C_{12}$-alkyl, $C_1$-$C_6$-alkoxy, $C_1$-$C_4$-haloalkyl or $C_1$-$C_4$-haloalkoxy, $V^2$ likewise preferably represents hydrogen, halogen, $C_1$-$C_6$-alkyl, $C_1$-$C_6$-alkoxy or $C_1$-$C_4$-haloalkyl, $V^1$ and $V^2$ together likewise preferably represent $C_3$-$C_4$-alkanediyl which may optionally be substituted by halogen and/or $C_1$-$C_2$-alkyl and which may optionally be interrupted by one or two oxygen atoms, W moreover preferably represents hydrogen, methyl, propyl, isopropyl or halogen, X moreover preferably represents halogen, $C_1$-$C_6$-alkyl, $C_1$-$C_6$-alkoxy, $C_1$-$C_4$-haloalkyl, $C_1$-$C_4$-haloalkoxy or cyano, Y in the 3- or 5-position moreover preferably represents hydrogen, halogen or $C_1$-$C_6$-alkyl, Z in the 4-position moreover preferably represents hydrogen, halogen, $C_1$-$C_6$-alkyl, $C_1$-$C_4$-haloalkyl, cyano or $C_1$-$C_4$-haloalkoxy, A preferably represents an optionally $C_1$-$C_4$-alkyl-substituted $C_1$-$C_4$-alkanediyl group or represents optionally $C_1$-$C_4$-alkyl-substituted $C_5$-$C_8$-cycloalkyl in which optionally one methylene group is replaced by oxygen, B preferably represents optionally halogen-substituted $C_2$-$C_8$-alkenyl, $C_1$-$C_6$-alkoxy, $C_1$-$C_6$-alkoxy-$C_1$-$C_4$-alkyloxy, represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl, represents optionally halogen-, $C_1$-$C_4$-alkyl- or $C_1$-$C_2$-haloalkyl-substituted pyridyl, pyrimidyl, thiazolyl or thienyl or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which optionally one or two not directly adjacent methylene groups are replaced by oxygen or three methylene groups are replaced by the radical —O—CO—O—, D preferably represents NH or oxygen, G preferably represents hydrogen (a) or represents one of the groups

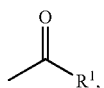
(b)

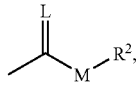
(c)

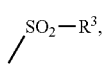
(d)

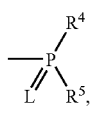
(e)

E or
(f)

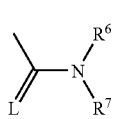
(g)

in which

E represents a metal ion or an ammonium ion,

L represents oxygen or sulphur and

M represents oxygen or sulphur.

$R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$- cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen.

$R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine W particularly preferably represents $C_1$-$C_4$-alkyl or $C_1$-$C_4$-alkoxy, X particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 4-position particularly preferably represents hydrogen, chlorine, bromine, cyano or trifluoromethyl, Z particularly preferably represents hydrogen, W also particularly preferably represents hydrogen, chlorine, bromine or $C_1$-$C_4$-alkyl, X also particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 4-position also particularly preferably represents the radical

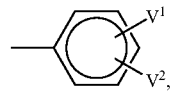

Z also particularly preferably represents hydrogen, $V^1$ also particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ also particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together also particularly preferably represent —O—$CH_2$—O— and —O—$CF_2$—O—.

W likewise particularly preferably represents hydrogen or $C_1$-$C_4$-alkyl,

X likewise particularly preferably represents chlorine, $C_1$-$C_4$-alkyl or $C_1$-$C_2$-haloalkyl, Y in the 5-position likewise particularly preferably represents the radical

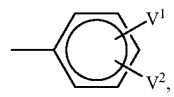

Z in the 4-position likewise particularly preferably represents hydrogen, $C_1$-$C_4$-alkyl or chlorine.

$V^1$ likewise particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ likewise particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together likewise particularly preferably represent —O—$CH_2$—O— or —O—$CF_2$—O—, W moreover particularly preferably represents hydrogen, methyl, chlorine or bromine, X moreover particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 3- or 5-position moreover particularly preferably represents hydrogen, chlorine, bromine or $C_1$-$C_4$-alkyl, Z in the 4-position moreover particularly preferably represents hydrogen, chlorine, bromine, $C_1$-$C_4$-alkyl, $C_1$-$C_2$-haloalkyl, cyano or $C_1$-$C_2$-haloalkoxy, A particularly preferably represents an optionally $C_1$-$C_2$-alkyl-substituted $C_1$-$C_3$-alkanediyl group or represents $C_5$-$C_6$-cycloalkyl in which optionally a methylene group is replaced by oxygen, B particularly preferably represents $C_2$-$C_6$-alkenyl, $C_1$-$C_4$-alkoxy, $C_1$-$C_4$-alkoxy-$C_1$-$C_3$-alkyloxy, each of which is optionally mono- to trisubstituted by fluorine or chlorine, represents phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, represents pyridyl, pyrimidyl, thiazolyl or thienyl, each of which is optionally mono- or disubstituted by fluorine, chlorine, bromine, methyl, ethyl or trifluoromethyl or represents $C_3$-$C_6$-cycloalkyl which is optionally mono- or disubstituted by fluorine, chlorine, methyl, methoxy or trifluoromethyl and in which optionally one methylene group is replaced by oxygen or three methylene groups are replaced by the radical —O—CO—O—, D particularly preferably represents NH, G particularly preferably represents hydrogen (a) or represents one of the groups

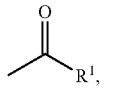 (b)

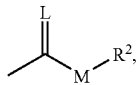 (c)

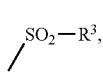 (d)

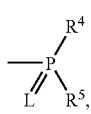 (e)

E or (f)

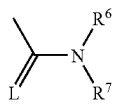 (g)

in which
E represents a metal ion or an ammonium ion,
L represents oxygen or sulphur and
M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyl-oxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine, or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy or together represent a $C_3$-$C_6$-alkylene radical which is optionally substituted by $C_1$-$C_4$-alkyl and in which optionally one methylene group is replaced by oxygen or sulphur.

In the radical definitions mentioned as being particularly preferred, halogen represents fluorine, chlorine and bromine, in particular fluorine and chlorine.

W very particularly preferably represents ethyl or methoxy,

X very particularly preferably represents chlorine, bromine, methyl, ethyl, propyl, methoxy, trifluoromethyl, difluoromethoxy, trifluoroethoxy or cyano, Y in the 4-position very particularly preferably represents hydrogen, chlorine or bromine, Z very particularly preferably represents hydrogen, W also very particularly preferably represents hydrogen, chlorine, bromine or methyl, X also very particularly preferably represents chlorine, bromine, methyl, ethyl, propyl, methoxy, trifluoromethyl, difluoromethoxy or cyano, Y in the 4-position also very particularly preferably represents the radical

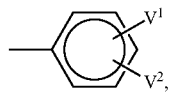

Z also very particularly preferably represents hydrogen, $V^1$ also very particularly preferably represents fluorine, chlorine, methyl, methoxy, trifluoromethyl or trifluoromethoxy, $V^2$ also very particularly preferably represents hydrogen, fluorine, chlorine, methyl, methoxy or trifluoromethyl, W likewise very particularly preferably represents hydrogen or methyl, X likewise very particularly preferably represents chlorine, methyl or trifluoromethyl, Y in the 5-position likewise very particularly preferably represents the radical

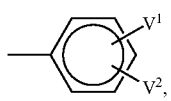

Z in the 4-position likewise very particularly preferably represents hydrogen or methyl, $V^1$ likewise very particularly preferably represents fluorine, chlorine, methyl, methoxy, trifluoromethyl or trifluoromethoxy, $V^2$ likewise very particularly preferably represents hydrogen, fluorine, chlorine, methyl, methoxy or trifluoromethyl, W moreover very particularly preferably represents hydrogen, methyl, chlorine or bromine, X moreover very particularly preferably represents chlorine, bromine, methyl, ethyl, propyl, methoxy, trifluoromethyl, difluoromethoxy, trifluoroethoxy or cyano, Y in the 3- or 5-position moreover very particularly preferably represents hydrogen, chlorine, bromine or methyl, Z in the 4-position moreover very particularly preferably represents hydrogen, chlorine, bromine, methyl, trifluoromethyl or trifluoromethoxy, A very particularly preferably represents —$CH_2$—, —$CHCH_3$—, —$CH_2$—$CH_2$—, —$CH_2$—$CH_2$—$CH_2$—, B very particularly preferably represents $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen, D very particularly preferably represents NH, G very particularly preferably represents hydrogen (a) or represents one of the groups

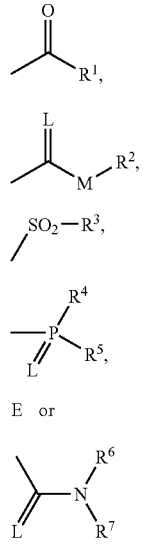

in which
E represents a metal ion or an ammonium ion,
L represents oxygen or sulphur and
M represents oxygen or sulphur, $R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, i-propyl, methoxy, ethoxy, trifluoromethyl or trifluoromethoxy, represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl or represents phenyl or benzyl, each of which is optionally mono- or disubstituted by fluorine, chlorine, cyano, nitro, methyl, ethyl, methoxy, trifluoromethyl or trifluoromethoxy, $R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl or together represent a $C_5$-$C_6$-alkylene radical in which optionally one methylene group is replaced by oxygen or sulphur.

W especially preferably represents ethyl or methoxy,

X especially preferably represents chlorine, bromine, methyl, ethyl, propyl, methoxy, trifluoromethyl, difluoromethoxy or cyano, Y in the 4-position especially preferably represents hydrogen, chlorine or bromine, Z in the 5-position especially preferably represents hydrogen, A especially preferably represents —$CH_2$—, —$CHCH_3$— or —$CH_2$—$CH_2$—, B especially preferably represents $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, cyclopentyl or cyclohexyl in which optionally one methylene group is replaced by oxygen, D especially preferably represents NH, G especially preferably represents hydrogen (a) or represents one of the groups

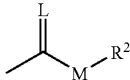

in which
L represents oxygen and
M represents oxygen or sulphur,

R¹ especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl,
represents phenyl which is optionally monosubstituted by fluorine, chlorine, bromine, cyano, nitro, methyl, methoxy, trifluoromethyl or trifluoromethoxy,
represents furanyl, thienyl or pyridyl, each of which is optionally monosubstituted by chlorine or methyl, R² especially preferably represents $C_1$-$C_8$-alkyl, $C_2$-$C_6$-alkenyl or $C_1$-$C_2$-alkoxy-$C_2$-$C_3$-alkyl,
represents cyclopentyl or cyclohexyl,
or represents phenyl or benzyl, each of which is optionally monosubstituted by fluorine, chlorine, cyano, nitro, methyl, methoxy, trifluoromethyl or trifluoromethoxy.

W also especially preferably represents hydrogen, chlorine, bromine or methyl,
X also especially preferably represents chlorine, bromine, methyl, ethyl, propyl, methoxy, trifluoromethyl, difluoromethoxy or cyano,
Y in the 4-position also especially preferably represents the radical

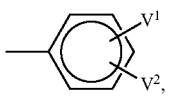

Z also especially preferably represents hydrogen,
V¹ also especially preferably represents fluorine, chlorine, methyl, methoxy, trifluoromethyl or trifluoromethoxy,
V² also especially preferably represents hydrogen, fluorine, chlorine, methyl, methoxy or trifluoromethyl,
A also especially preferably represents —$CH_2$—, —$CHCH_3$— or —$CH_2$—$CH_2$—,
B also especially preferably represents $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro,
D also especially preferably represents NH,
G also especially preferably represents hydrogen (a) or represents one of the groups

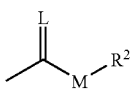

in which
L represents oxygen and
M represents oxygen or sulphur,

R¹ also especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl,
represents phenyl which is optionally monosubstituted by fluorine, chlorine, bromine, cyano, nitro, methyl, methoxy, trifluoromethyl or trifluoromethoxy,
represents furanyl, thienyl or pyridyl, each of which is optionally monosubstituted by chlorine or methyl, R² also especially preferably represents $C_1$-$C_8$-alkyl, $C_2$-$C_6$-alkenyl or $C_1$-$C_2$-alkoxy-$C_2$-$C_3$-alkyl,
represents cyclopentyl or cyclohexyl,
or represents phenyl or benzyl, each of which is optionally monosubstituted by fluorine, chlorine, cyano, nitro, methyl, methoxy, trifluoromethyl or trifluoromethoxy.

W likewise especially preferably represents hydrogen or methyl,
X likewise especially preferably represents chlorine or methyl,
Y in the 5-position likewise especially preferably represents the radical

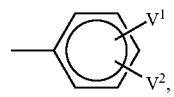

Z in the 4-position likewise especially preferably represents hydrogen or methyl,
V¹ likewise especially preferably represents fluorine, chlorine, methyl, methoxy, trifluoromethyl or trifluoromethoxy,
V² likewise especially preferably represents hydrogen, fluorine, chlorine, methyl, methoxy or trifluoromethyl,
A likewise especially preferably represents —$CH_2$—, —$CHCH_3$— or —$CH_2$—$CH_2$—,
B likewise especially preferably represents $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro,
D likewise especially preferably represents NH,
G likewise especially preferably represents hydrogen (a) or represents one of the groups

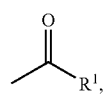

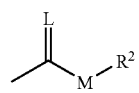

in which
L represents oxygen and
M represents oxygen or sulphur,

R¹ likewise especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl, represents phenyl which is optionally monosubstituted by fluorine, chlorine, bromine, cyano, nitro, methyl, methoxy, trifluoromethyl or trifluoromethoxy, represents furanyl, thienyl or pyridyl, each of which is optionally monosubstituted by chlorine or methyl, $R^2$ likewise especially preferably represents $C_1$-$C_8$-alkyl, $C_2$-$C_6$-alkenyl or $C_1$-$C_2$-alkoxy-$C_2$-$C_3$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy.

W moreover especially preferably represents hydrogen, methyl, chlorine or bromine, X moreover especially preferably represents chlorine, bromine, methyl, ethyl, methoxy, trifluoromethyl, difluoromethoxy or cyano, Y in the 3- or 5-position moreover especially preferably represents hydrogen, chlorine, bromine or methyl, Z in the 4-position moreover especially preferably represents hydrogen, chlorine, bromine, methyl, trifluoromethyl or trifluoromethoxy, A moreover especially preferably represents —$CH_2$—, —$CHCH_3$— or —$CH_2$—$CH_2$—, B moreover especially preferably represents $C_2$-$C_4$-alkenyl, methoxy, ethoxy, propoxy, isopropoxy, butoxy, isobutoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen, D moreover especially preferably represents NH, G moreover especially preferably represents hydrogen (a) or represents one of the groups

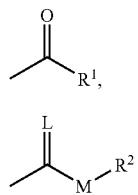

in which

L represents oxygen and

M represents oxygen or sulphur, $R^1$ moreover especially preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents cyclopropyl, cyclopentyl or cyclohexyl, represents phenyl which is optionally monosubstituted by fluorine, chlorine, bromine, cyano, nitro, methyl, methoxy, trifluoromethyl or trifluoromethoxy, represents furanyl, thienyl or pyridyl, each of which is optionally monosubstituted by chlorine or methyl, $R^2$ moreover especially preferably represents $C_1$-$C_{10}$-alkyl, $C_2$-$C_{10}$-alkenyl or $C_1$-$C_2$-alkoxy-$C_2$-$C_4$-alkyl, represents cyclopentyl or cyclohexyl, or represents phenyl or benzyl, each of which is optionally monosubstituted by fluorine, chlorine, cyano, nitro, methyl, methoxy, trifluoromethyl or trifluoromethoxy.

W most preferably represents hydrogen,

X most preferably represents methyl or chlorine,

Y in the 5-position most preferably represents chlorine-substituted phenyl,

Z most preferably represents hydrogen,

A most preferably represents —$CH_2$—,

B most preferably represents chlorine-substituted phenyl,

D most preferably represents NH,

G most preferably represents hydrogen.

W moreover most preferably represents hydrogen or methyl,

X moreover most preferably represents methyl or chlorine,

Y in the 3- or 5-position moreover most preferably represents hydrogen or methyl, Z in the 4-position moreover most preferably represents hydrogen, methyl or chlorine, A moreover most preferably represents —$CH_2$— or —$CH_2$—$CH_2$—, B moreover most preferably represents methoxy, ethoxy, isopropyl, cyclopentyl in which optionally one methylene group is replaced by oxygen, cyclohexyl, ethenyl or represents optionally chlorine-substituted phenyl, D moreover most preferably represents NH, G moreover most preferably represents hydrogen (a) or represents one of the groups

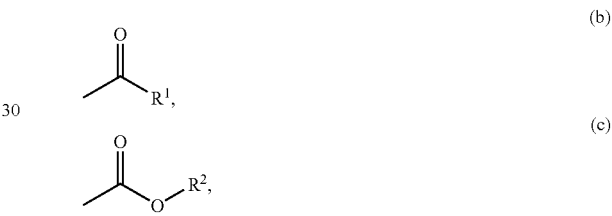

$R^1$ moreover most preferably represents $C_1$-$C_6$-alkyl, $R^2$ moreover most preferably represents $C_1$-$C_6$-alkyl.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Most preference according to the invention is given to the compounds of the formula (I) which contain a combination of the meanings listed above as being most preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitutions the substituents can be identical or different.

Using, for example, according to process (A) ethyl N-[(4-chloro-2,6-dimethyl)-phenylacetyl]-1-amino-4-allyloxycyclohexanecarboxylate as starting material, the course of the process according to the invention can be represented by the reaction scheme below:

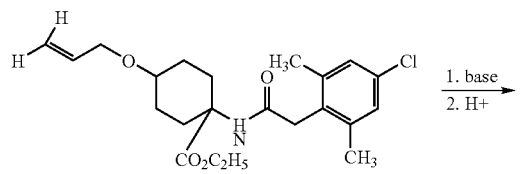

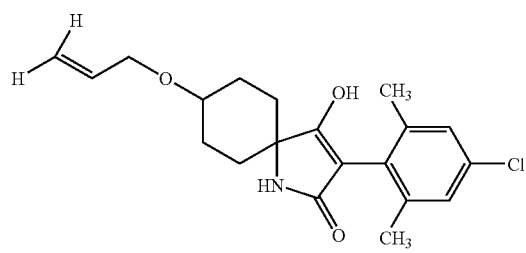

Using, for example, according to process (B) ethyl O-[(2-chloro-6-methyl)-phenylacetyl]-1-hydroxy-4-benzyloxycyclohexanecarboxylate as starting material, the course of the process according to the invention can be represented by the reaction scheme below:

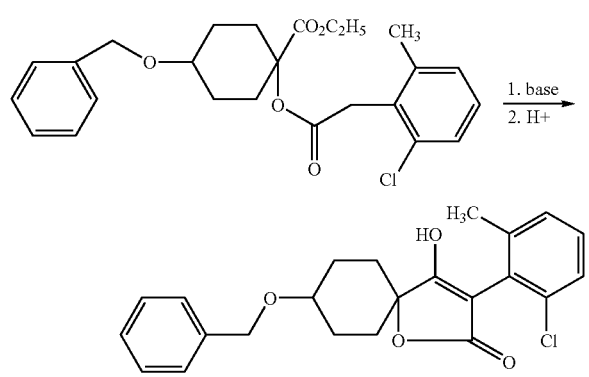

Using, for example, according to process (Cα) 3-[(4-chloro-2,6-dimethyl)phenyl]-5,5-(3-allyloxypentamethylenediyl)pyrrolidine-2,4-dione and pivaloyl chloride as starting materials, the course of the process according to the invention can be represented by the reaction scheme below:

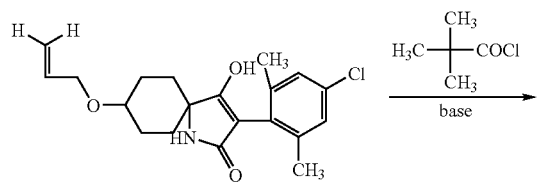

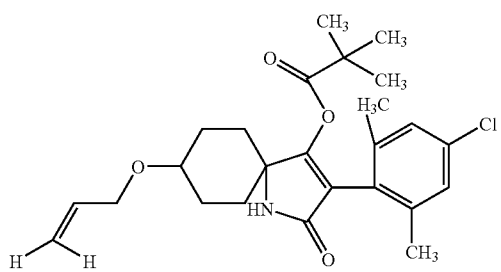

Using, for example, according to process (C) (variante β) 3-[(2,4-dichloro)phenyl]-4-hydroxy-5,5-(3-benzyloxypentamethylenediyl)-Δ³-dihydrofuran-2-one and acetic anhydride as starting materials, the course of the process according to the invention can be represented by the reaction scheme below:

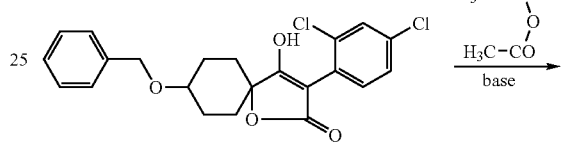

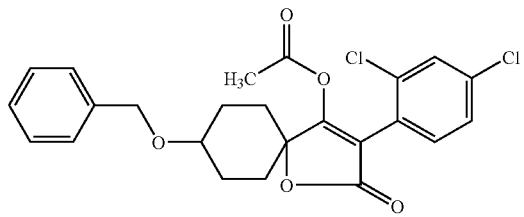

Using, for example, according to process (D) 8-[(2,4-dichloro-6-methyl)phenyl]-5,5-(3-allyloxypentamethylenediyl)pyrrolidine-2,4-dione and ethoxyethyl chloroformate as starting materials, the course of the process according to the invention can be represented by the reaction scheme below:

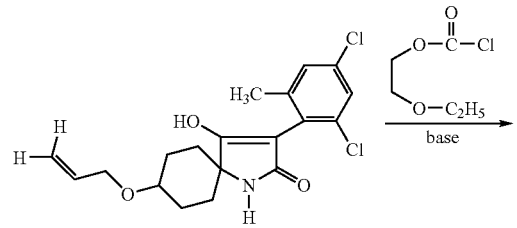

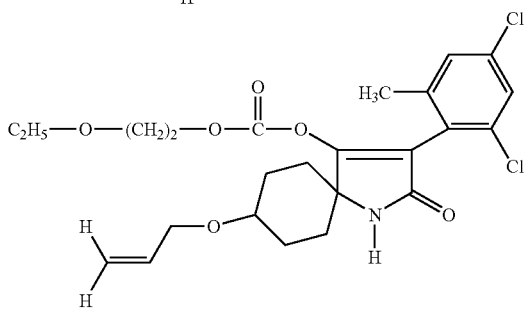

Using, for example, according to process (E) 3[(2,4,6-trimethyl)phenyl]-4-hydroxy-5,5-(3-benzyloxypentamethylenediyl)-Δ³-dihydrofuran-2-one and methyl chloro-monothioformate as starting materials, the course of the reaction can be represented as follows:

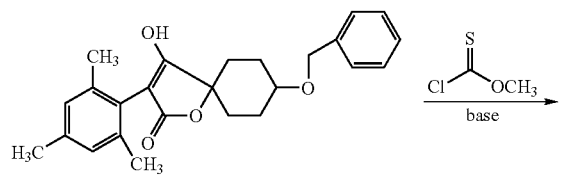
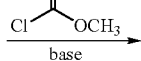
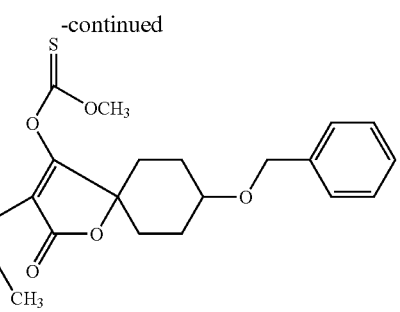

Using, for example, according to process (F) 2-[2,4,6-trimethyl)phenyl]-5,5-[3-(4-chloro)benzyloxypentamethylenediyl]pyrrolidine-2,4-dione and methanesulphonyl chloride as starting materials, the course of the reaction can be represented by the reaction scheme below:

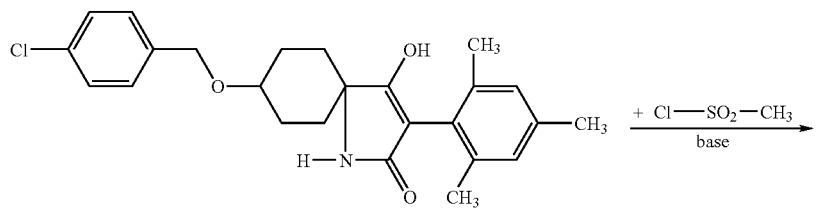

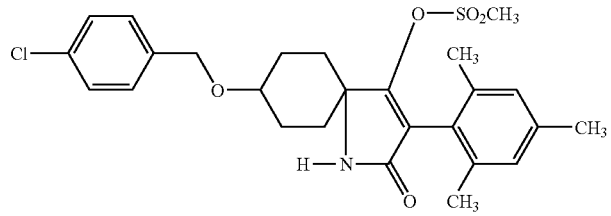

Using, for example, according to process (G) 2[(2,4-dichloro-6-methyl)phenyl]-4-hydroxy-5,5-(3-benzyloxypentamethylenediyl)-Δ³-dihydrofuran-2-one and 2,2,2-trifluoroethyl methanethiophosphonyl chloride as starting materials, the course of the reaction can be represented by the reaction scheme below:

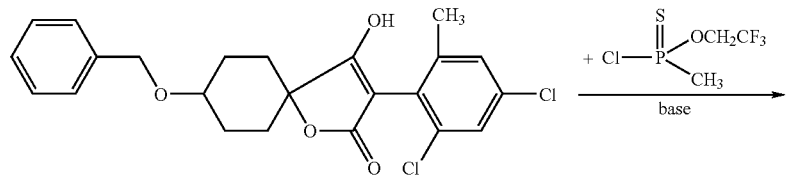

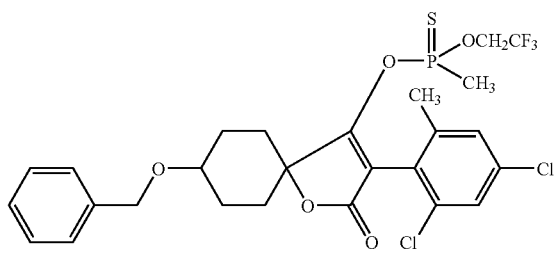

Using, for example, according to process (H) 3-(2,3,4,6-tetramethylphenyl)-5,5-(3-methoxyethyloxypentamethylenediyl)-pyrrolidine-2,4-dione and NaOH as components, the course of the process according to the invention can be represented by the reaction scheme below:

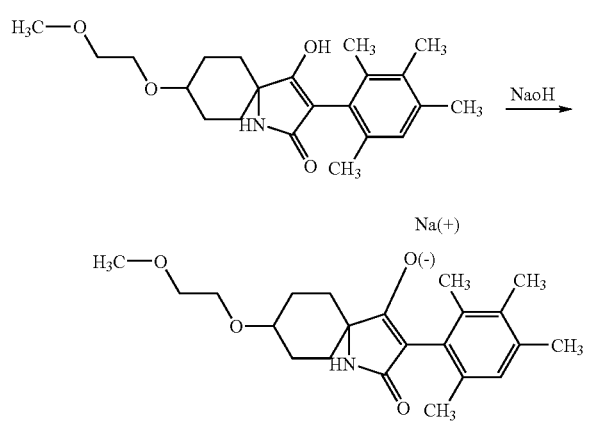

Using, for example, according to process (I) (variant α) 3[(2,4,5-trimethyl)phenyl]-4-hydroxy-5,5-(3-benzyloxy-pentamethylenediyl)-Δ³-dihydrofuran-2-one and ethyl isocyanate as starting materials, the course of the reaction can be represented by the reaction scheme below:

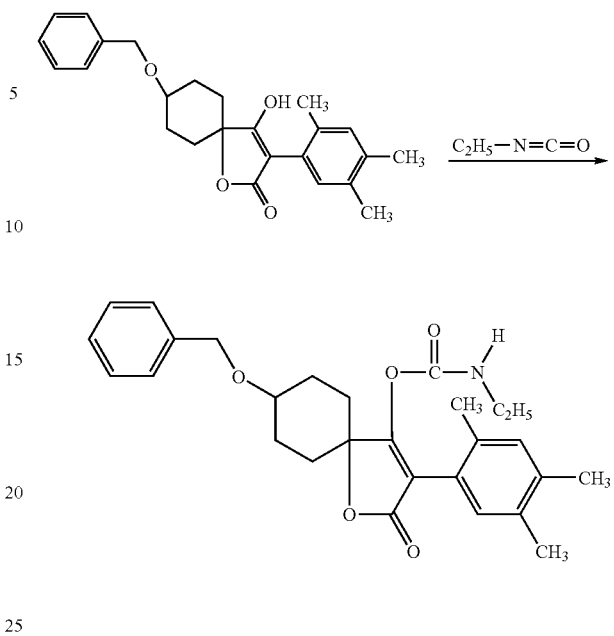

Using, for example, according to process (I) (variante β) 3[(2,4,6-trimethyl)phenyl]-5,5-[3-(3-chloro)benzyloxypentamethylenediyl]pyrrolidine-2,4-dione and dimethylcarbamoyl chloride as starting materials, the course of the reaction can be represented by the scheme below:

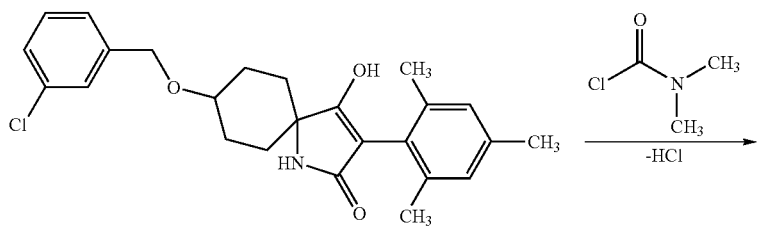

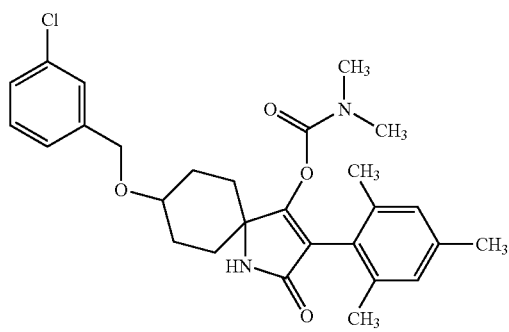

The compounds, required as starting materials for the process (A) according to the invention, of the formula (II),

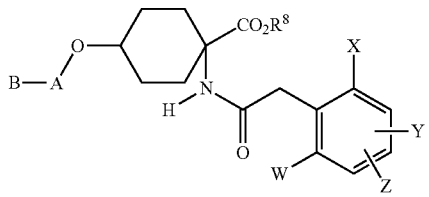
(II)

in which
A, B, W, X, Y, Z and $R^8$ are as defined above,
are novel.

The acylamino acid esters of the formula (II) are obtained, for example, when amino acid derivatives of the formula (XIV),

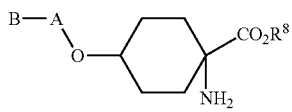
(XIV)

in which
A, B and $R^8$ are as defined above
are acylated with substituted phenyl acetyl halides of the formula (XV),

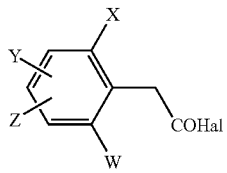
(XV)

in which
W, X, Y and Z are as defined above and
Hal represents chlorine or bromine
(Chem. Reviews 52, 237-416 (1953); Bhattacharya, Indian J. Chem. 6, 341-5, 1968),
or when acylamino acids of the formula (XVI),

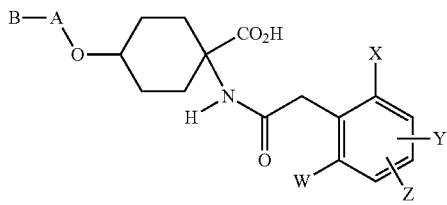
(XVI)

in which
A, B, W, X, Y and Z are as defined above
are esterified (Chem. Ind. (London) 1568 (1968)).

The compounds of the formula (XVI),

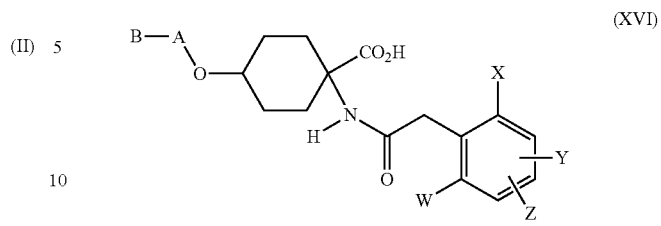
(XVI)

in which
A, B, W, X, Y and Z are as defined above
are novel.

The compounds of the formula (XVI) are obtained, for example, when 1-aminocyclohexanecarboxylic acids of the formula (XVII),

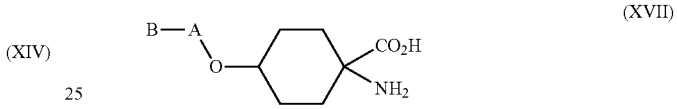
(XVII)

in which
A and B are as defined above
are acylated according to Schotten-Baumann with substituted phenylacetyl halides of the formula (XV),

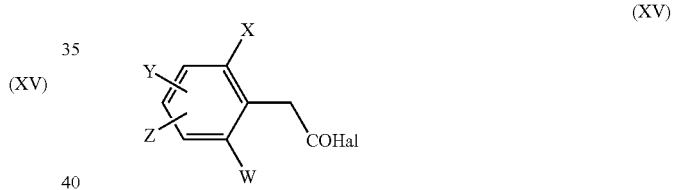
(XV)

in which
W, X, Y and Z are as defined above and
Hal represents chlorine or bromine
(Organikum, VEB Deutscher Verlag der Wissenschaften, Berlin 1977, p. 505).

Some of the compounds of the formula (XV) are known and/or can be prepared by the known processes in the laid-open documents cited at the outset.

The compounds of the formulae (XIV) and (XVII) are novel and can be prepared according to known processes (see, for example, Compagnon, Ann. Chim (Paris) [14] 5, p. 11-22, 23-27 (1970), L. Munday, J. Chem. Soc. 4372 (1961); J. T. Eward, C. Jitrangeri, Can. J. Chem. 53, 3339 (1975).

The 1-aminocyclohexanecarboxylic acids (XVII) are novel and can generally be obtained by the Bucherer-Bergs synthesis or by the Strecker synthesis, where they are obtained in different isomeric forms. Thus, under the conditions of the Bucherer-Bergs synthesis, the isomer that is mainly obtained is the isomer (hereinbelow for the sake of simplicity referred to as β) in which the 4-substituent and the carboxyl group are in equatorial positions, whereas the conditions of the Strecker synthesis give mainly the isomer (hereinbelow for the sake of simplicity referred to as α) in which the amino group and the 4-substituent are in equatorial positions.

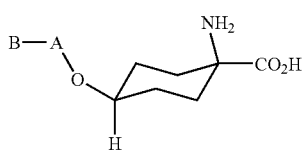

Bucherer-Bergs synthesis
(β isomer)

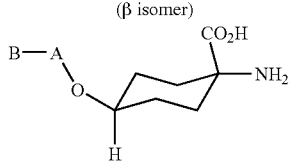

Strecker synthesis
(α isomer)

(L. Munday, J. Chem. Soc. 4372 (1961); J. T. Eward, C. Jitrangeri, Can. J. Chem. 53, 3339 (1975).

The starting materials, used in process (A) above, of the formula (II),

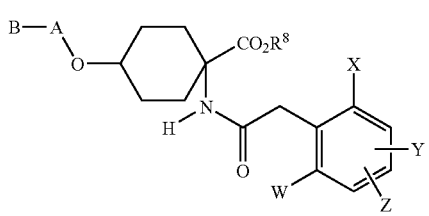
(II)

in which
A, B, W, X, Y, Z and $R^8$ are as defined above
can furthermore be prepared when 1-aminocyclohexanecarbonitriles of the formula (XVIII),

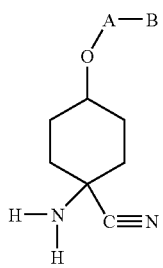
(XVIII)

in which
A and B are as defined above
are reacted with substituted phenylacetyl halides of the formula (XV),

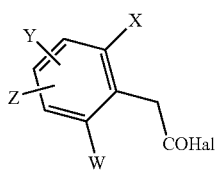
(XV)

in which
W, X, Y, Z and Hal are as defined above, to give compounds of the formula (XIX),

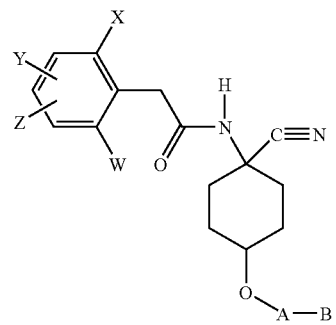
(XIX)

in which
A, B, W, X, Y and Z are as defined above,
and these are subsequently subjected to acid alcoholysis.

The compounds of the formula (XIX) are likewise novel.
The compounds of the formula (XVIII) are likewise novel.

The compounds, required as starting materials for the process (B) according to the invention, of the formula (III),

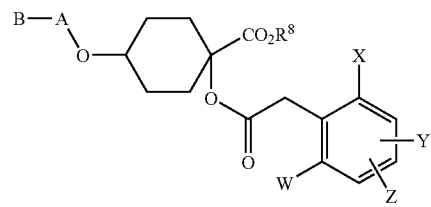
(III)

in which
A, B, W, X, Y, Z and $R^8$ are as defined above,
are novel.

They can be prepared in a simple manner by methods known in principle.

The compounds of the formula (III) are obtained, for example, when 1-hydroxycyclohexanecarboxylic acid esters of the formula (XX),

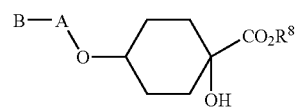
(XX)

in which
A, B and $R^8$ are as defined above,
are acylated with substituted phenylacetyl halides of the formula (XV),

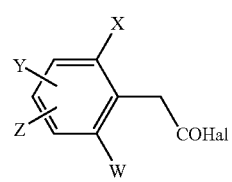

in which
W, X, Y, Z and Hal are as defined above
(Chem. Reviews 52, 237-416 (1953)).

Some of the 1-hydroxycyclohexylcarboxylic acid esters of the formula (XX) are novel. They are obtained, for example, by reacting substituted 1-hydroxycyclohexanecarbonitriles in the presence of acids, for example according to Pinner, with alcohols. The cyanohydrin is obtained, for example, by reaction of substituted cyclohexan-1-ones with hydrogen cyanide.

The acid halides of the formula (IV), carboxylic anhydrides of the formula (V), chloroformic esters or chloroformic thioesters of the formula (VI), chloromonothioformic esters or chlorodithioformic esters of the formula (VII), sulphonyl chlorides of the formula (VIII), phosphorus compounds of the formula (IX) and metal hydroxides, metal alkoxides or amines of the formula (X) and (XI), respectively, and isocyanates of the formula (XII) and carbamoyl chlorides of the formula (XIII) furthermore required as starting materials for carrying out the processes (C), (D), (E), (F), (G), (H) and (I) according to the invention are generally known compounds of organic or inorganic chemistry.

The compounds of the formula (XV) are furthermore known from the patent applications cited at the outset and/or can be prepared by the methods given therein.

The process (A) is characterized in that compounds of the formula (II) in which A, B, W, X, Y, Z and $R^8$ are as defined above are subjected to an intramolecular condensation in the presence of a diluent and in the presence of a base.

Suitable diluents for the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltri($C_8$-$C_{10}$) alkylammonium chloride) or TDA 1 (=tris(methoxyethoxyethyl)amine). It is furthermore possible to use alkali metals, such as sodium or potassium. It is further possible to use alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

When carrying out the process (A) according to the invention, the reaction temperature can be varied within a relatively wide range. In general, the process is carried out at temperatures between −75° C. and 200° C., preferably between −50° C. and 150° C.

The process (A) according to the invention is generally carried out under atmospheric pressure.

When carrying out the process (A) according to the invention, the reaction component of the formula (II) and the deprotonating base are generally employed in equimolar to about doubly equimolar amounts. However, it is also possible to use a relatively large excess (up to 3 mol) of one component or the other.

The process (B) is characterized in that compounds of the formula (III) in which A, B, W, X, Y, Z and $R^8$ are as defined above are condensed intramolecularly in the presence of a diluent and in the presence of a base.

Suitable diluents for the process (B) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltri($C_8$-$C_{10}$) alkylammonium chloride) or TDA 1 (=tris(methoxyethoxyethyl)amine). It is furthermore possible to use alkali metals, such as sodium or potassium. Alkali metal and alkaline earth metal amides and hydrides, such as sodium amide, sodium hydride and calcium hydride, and moreover also alkali metal alkoxides, such as sodium methoxide, sodium ethoxide and potassium tert-butoxide, can furthermore be used.

When carrying out the process (B) according to the invention, the reaction temperature can be varied within a relatively wide range. In general, the process is carried out at temperatures between −75° C. and 200° C., preferably between −50° C. and 150° C.

The process (B) according to the invention is generally carried out at atmospheric pressure.

When carrying out the process (B) according to the invention, the reaction components of the formula (III) and the deprotonating bases are generally employed in about equimolar amounts. However, it is also possible to use a relatively large excess (up to 3 mol) of one component or the other.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process ($C_\alpha$) according to the invention are all solvents which are inert to the acid halides. Preference is given to using hydrocarbons, such as benzine, benzene, toluene, xylene and Tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, and also strongly polar solvents, such as dimethylformamide, dimethyl sulphoxide and sulpholane. The hydrolytic stability of the acid halide permitting, the reaction can also be carried out in the presence of water.

Suitable acid binders for the reaction according to process ($C_\alpha$) according to the invention are all customary acid acceptors. Preference is given to using tertiary amines, such as triethylamine, pyridine, diazabicyclooctane (DABCO), diazabicycloundecene (DBU), diazabicyclonones (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process ($C_\alpha$) according to the invention can be varied within a relatively wide range. In general, the process is carried out at temperatures between −20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Suitable diluents for the process ($C_\beta$) according to the invention are, preferably, those diluents which are also preferred when acid halides are used. Furthermore, it is also possible for a carboxylic anhydride used in excess to act simultaneously as diluent.

Suitable acid binders, which are added, if appropriate, for process ($C_\beta$) are, preferably, those acid binders which are also preferred when acid halides are used.

The reaction temperature in the process ($C_\beta$) according to the invention can be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable acid binders for the process (D) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and alkali metal hydroxides, such as sodium hydroxide and potassium hydroxide.

Suitable diluents for the process (D) according to the invention are all solvents which are inert to the chloroformic esters or chloroformic thioesters. Preference is given to using hydrocarbons, such as benzine, benzene, toluene, xylene and Tetralin; furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, moreover nitriles, such as acetonitrile, and also strongly polar solvents, such as dimethyl formamide, dimethyl sulphoxide and sulpholane.

When carrying out the process (D) according to the invention, the reaction temperature can be varied within a relatively wide range. The reaction temperature is generally between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the corresponding chloroformic ester or chloroformic thioester of the formula (VI) are generally each employed in approximately equivalent amounts. However, it is also possible to use the relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In the preparation process (E), about 1 mol of chloromonothioformic ester or chlorodithioformic ester of the formula (VII) is employed per mole of starting material of the formulae (I-1-a) to (I-2-a), at from 0 to 120° C., preferably at from 20 to 60° C.

Suitable diluents, which are added, if appropriate, are all inert polar organic solvents, such as ethers, amides, sulphones, sulphoxides, but also halogenated alkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by adding strong deprotonating agents, such as, for example, sodium hydride or potassium tert-butoxide, the further addition of acid binders can be dispensed with.

Suitable bases for process (E) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure and is preferably carried out under atmospheric pressure. The work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In preparation process (F), about 1 mol of sulphonyl chloride of the formula (VIII) is employed per mole of starting material of the formula (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethylformamide, ethyl acetate, methylene chloride.

If, in a preferred embodiment, the enolate salt of the compounds (I-1-a) to (I-2-a) is prepared by adding strong deprotonating agents (such as, for example, sodium hydride or potassium tert-butoxide), the further addition of acid binders can be dispensed with.

If acid binders are used, these may be customary inorganic or organic bases, for example sodium hydroxide, sodium carbonate or potassium carbonate, pyridine and triethylamine.

The reaction can be carried out under atmospheric pressure or under elevated pressure and is preferably carried out under atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In preparation process (G), to obtain compounds of the formulae (I-1-e) to (I-2-e), from 1 to 2, preferably from 1 to 1.3, mol of the phosphorus compound of the formula (IX) are employed per mole of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Suitable acid binders, which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods of organic chemistry. The end products are preferably purified by crystallization, chromatographic purification or by incipient distillation, i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Suitable diluents for the process (H) according to the invention are, preferably, ethers, such as tetrahydrofuran, dioxane, diethyl ether, or else alcohols, such as methanol, ethanol, isopropanol, but also water. The process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In preparation process (Iα), about 1 mol of isocyanate of the formula (XII) is employed per mole of starting material of the formulae (I-1-a) to (I-2-a), at from 0 to 100° C., preferably from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Catalysts which may be used in a very advantageous manner are organotin compounds, such as, for example, dibutyltin dilaurate.

The process is preferably carried out under atmospheric pressure.

In preparation process (Iβ), about 1 mol of carbamoyl chloride of the formula (XIII) is employed per mole of starting material of the formulae (I-1-a) to (I-2-a), at from 0 to 150° C., preferably from 20 to 70° C.

Suitable diluents, which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, Oniscus asellus, Armadillidium vulgare and Porcellio scaber.

From the order of the Diplopoda, for example, Blaniulus guttulatus.

From the order of the Chilopoda, for example, Geophilus carpophagus and Scutigera spp.

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Acheta domesticus, Gryllotalpa spp., Locusta migratoria migratorioides, Melanoplus spp. and Schistocerca gregaria.

From the order of the Blattaria, for example, Blatta orientalis, Periplaneta americana, Leucophaea maderae, Blattella germanica.

From the order of the Dermaptera, for example, Forficula auricularia.

From the order of the Isoptera, for example, Reticulitermes spp.

From the order of the Phthiraptera, for example, Pediculus humanus corporis, Haematopinus spp., Linognathus spp., Trichodectes spp. and Damalinia spp.

From the order of the Thysanoptera, for example, Hercinothrips femoralis, Thrips tabaci, Thrips palmi and Franldiniella accidentalis.

From the order of the Heteroptera, for example, Eurygaster spp., Dysdercus intermedius, Piesma quadrata, Cimex lectularius, Rhodnius prolixus and Triatoma spp.

From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus spp., Macrosiphum avenae, Myzus spp., Phorodon humuli, Rhopalosiphum padi, Empoasca spp., Euscelis bilobatus, Nephotettix cincticeps, Lecanium corn, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Mamestra brassicae, Panolis flammea, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, ToMix viridana, Cnaphalocerus spp., Oulema oryzae.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica and Lissorhoptrus oryzophilus.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa, Hylemyia spp. and Liriomyza spp.

From the order of the Siphonaptera, for example, Xenopsylla cheopis and Ceratophyllus spp.

From the class of the Arachnida, for example, Scorpio maurus, Latrodectus mactans, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Hemitarsonemus spp., Brevipalpus spp.

The phytoparasitic nematodes include, for example, Pratylenchus spp., Radopholus similis, Ditylenchus dipsaci, Tylenchulus semipenetrans, Heterodera spp., Globodera spp., Meloidogyne spp., Aphelenchoides spp., Longidorus spp., Xiphinema spp., Trichodorus spp., Bursaphelenchus spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be employed as such or in their formulations as a mixture with known fungicides, bactericides, acaricides, nematicides or insecticides in order to increase the activity spectrum or avoid the development of resistance. In many cases synergistic effects are achieved, ie. the efficacy of the mixture is greater than the efficacy of the individual components.

Favourable examples of co-components in mixtures are the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
ediphenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl{2-methyl-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole, 1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-(3-D-glycopyranosyl)-α-D-glucopyranosyl]-amino]-4-methoxy-1H-pyrrolo[2,3-d]pyrimidine-5-carbonibile, 2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolol-1,5-alquinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[3-methylbenzoyl)-oxy]-2,5-thiophenedicarboxylate,
cis-1-(4-chlorophenyl)-2-(1H-1,2,4-triazol-1-yl)-cycloheptanol,
cis-4-β-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxymethanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[3,4-dimethoxyphenyl)-3-(4-fluorophenyl)-acryloyl]-morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, bistrifluoron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, Metharhizium anisopliae, metarhizium flavoviride, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, Verticillium lecanii,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-ylbutanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl-[2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as by a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with novel properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or widenings of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defense of the plants against insects by toxins formed in the plants, in particular those formed in the plants by the genetic material from Bacillus thuringiensis (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example Blatta orientalis, Periplaneta americana, Blattela germanica and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without limitation:

Beetles, such as
Hylotrupes bajulus, Chlorophorus pilosis, Anobium punctatum, Xestobium rufovillosum, Ptilinus pecticornis, Dendrobium pertinex, Ernobius mollis, niobium carpini, Lyctus brunneus, Lyctus africanus, Lyctus planicollis, Lyctus linearis, Lyctus pubescens, Trogoxylon aequale, Minthes rugicollis, Xyleborus spec. Tryptodendron spec. Apate monachus, Bostrychus capucins, Heterobostrychus brunneus, Sinoxylon spec. Dinoderus minutus.

Hymenopterons, such as
Sirex juvencus, Urocerus gigas, Urocerus gigas taignus, Urocerus augur.

Termites, such as
Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus. Bristletails, such as Lepisma saccharina.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:
building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably $\alpha$-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron,
and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., in particular fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb; or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleinimide The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, Buthus occitanus.

From the order of the Acarina, for example, Argas persicus, Argas reflexus, Bryobia ssp., Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.

From the order of the Araneae, for example, Aviculariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, Blaniulus guttulatus, Polydesmus spp.

From the order of the Chilopoda, for example, Geophilus spp.

From the order of the Zygentoma, for example, Ctenolepisma spp., Lepisma saccharina, Lepismodes inquilinus.

From the order of the Blattaria, for example, Blatta orientalies, Blattella germanica, Blattella asahinai, Leucophaea maderae, Panchlora spp., Parcoblatta spp., Periplaneta australasiae, Periplaneta americana, Periplaneta brunnea, Periplaneta fuliginosa, Supella longipalpa.

From the order of the Saltatoria, for example, Acheta domesticus.

From the order of the Dermaptera, for example, Forficula auricularia.

From the order of the Isoptera, for example, Kalotermes spp., Reticulitermes spp.

From the order of the Psocoptera, for example, Lepinatus spp., Liposcelis spp.

From the order of the Coleptera, for example, Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

From the order of the Diptera, for example, Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

From the order of the Lepidoptera, for example, Achroia grisella, Galleria mellonella, Plodia interpunctella, Tinea cloacella, Tinea pellionella, Tineola bisselliella.

From the order of the Siphonaptera, for example, Ctenocephalides canis, Ctenocephalides felis, Pulex irritans, Tunga penetrans, Xenopsylla cheopis.

From the order of the Hymenoptera, for example, Camponotus herculeanus, Lasius fuliginosus, Lasius niger, Lasius umbratus, Monomorium pharaonis, Paravespula spp., Tetramorium caespitum.

From the order of the Anoplura, for example, Pediculus humanus capitis, Pediculus humanus corporis, Phthirus pubis.

From the order of the Heteroptera, for example, Cimex hemipterus, Cimex lectularius, Rhodinus prolixus, Triatoma infestans.

In the field of household insecticides, they are used alone or in combination with other suitable active compounds, such as phosphoric acid esters, carbamates, pyrethroids, growth regulators or active compounds from other known classes of insecticide.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Photons, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example
acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropyl ammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example:
AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:
Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea
(conidia form: Drechslera, syn: Helminthosporium);
Cochliobolus species, such as, for example, Cochliobolus sativus
(conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The active compounds according to the invention also have very good fortifying action in plants. Accordingly, they can be used for mobilizing the defenses of the plant against attack by undesirable microorganisms.

In the present context, plant-fortifying (resistance-inducing) substances are to be understood as meaning those substances which are capable of stimulating the defense system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as Alternaria tenuis,
Aspergillus, such as Aspergillus niger,
Chaetomium, such as Chaetomium globosum,
Coniophora, such as Coniophora puetana,
Lentinus, such as Lentinus tigrinus,
Penicillium, such as Penicillium glaucum,
Polyporus, such as Polyporus versicolor,
Aureobasidium, such as Aureobasidium pullulans,
Sclerophoma, such as Sclerophoma pityophila,
Trichoderma, such as Trichoderma viride,
Escherichia, such as Escherichia coli,
Pseudomonas, such as Pseudomonas aeruginosa, and
Staphylococcus, such as Staphylococcus aureus.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:
Fungicides:
2-phenylphenol; 8-hyroxyquinoline sulphate;
acibenzolar-S-methyl; aldimorph; amidoflumet; ampropylfos; ampropylfos-potassium; andoprim; anilazine; azaconazole; azoxystrobin;
benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine;
calcium polysulphide; capsimycin; captafol; captan; carbendazim; carboxin; carpropamide; carvone; quinomethionate; chlobenthiazone; chlorfenazole; chloroneb; chlorothalonil; chlozolinate; clozylacon; cyazofamide; cyflufenamide; cymoxanil; cyproconazole; cyprodinil; cyprofuram;
dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;
edifenphos; epoxiconazole; ethaboxam; ethirimol; etridiazole; famoxadone; fenamidone; fenapanil; fenarimol; fenbuconazole; fenfuram; fenhexamide; fenitropan; fenoxanil; fenpiclonil; fenpropidin; fenpropimorph; ferbam; fluazinam; flubenzimine; fludioxanil; flumetover; flumorph; fluoromide; fluoxastrobin; fluquinconazole; flurprimidol; flusilazole; flusulfamide; flutolanil; flutriafol; folpet; fosetyl-aluminium; fosetyl-sodium; fuberidazole; furalaxyl; furametpyr; furcarbanil; furmecyclox;
guazatine;
hexachlorobenzene; hexaconazole; hymexazole;
imazalil; imibenconazole; iminoctadine triacetate; iminoctadine tris-albesil; iodocarb; ipconazole; iprobenfos; iprodione; iprovalicarb; irumamycin; isoprothiolane; isovaledione;
kasugamycin; kresoxim-methyl;
mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin;
natamycin; nicobifen; nitrothal-isopropyl; noviflumuron; nuarimol;
ofurace; orysastrobin; oxadixyl; oxolinic acid; oxpoconazole; oxycarboxin; oxyfenthiin;
paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrroInitrine;
quinconazole; quinoxyfen; quintozene;
simeconazole; spiroxamine; sulphur;
tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;
uniconazole;
validamycin A; vinclozolin;
zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]butanamide;
1-(1-naphthalenyl)-1H-pyrrole-2,5-dione;
2,3,5,6-tetrachloro-4-(methylsulphonyl)pyridine;
2-amino-4-methyl-N-phenyl-5-thiazolecarboxamide;
2-chloro-N-(2,3-dihydro-1,1,3-trimethyl-1H-inden-4-yl)-3-pyridinecarboxamide;
3,4,5-trichloro-2,6-pyridinedicarbonitrile;
Actinovate;
cis-1-(4-chlorophenyl)-2-(1H-1,2,4-triazol-1-yl)-cycloheptanol;
methyl 1-(2,3-dihydro-2,2-dimethyl-1H-inden-1-yl)-1H-imidazole-5-carboxylate; monopotassium carbonate;
N-(6-methoxy-3-pyridinyl)cyclopropanecarboxamide;
N-butyl-8-(1,1-dimethylethyl)-1-oxaspiro[4.5]decan-3-amine;
sodium tetrathiocarbonate;
and copper salts and copper preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, Metharhizium anisopliae, Metharhizium flavoviride, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
Paecilomyces fumosoroseus, parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, Verticillium lecanii, YI 5302 zeta-cypermethrin, zolaprofos (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-ylbutanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridin-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against Candida species, such as Candida albicans, Candida glabrata), and Epidermophyton floccosum, Aspergillus species, such as Aspergillus niger and Aspergillus fumigatus, Trichophyton species, such as Trichophyton mentagrophytes, Microsporon species such as Microsporon canis and audouinii. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The preparation and the use of the active compounds according to the invention is illustrated by the examples below.

PREPARATION EXAMPLES

Example I-1-a-1

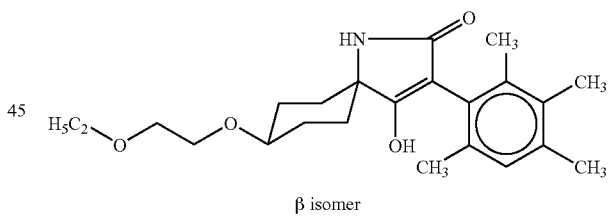

β isomer

At 80° C., 1.5 g (36 mmol) of the compound of Preparation Example II-1 in 5 ml of anhydrous dimethylformamide are added dropwise to 1 g (90 mmol) of potassium tert-butoxide in 10 ml of anhydrous dimethylformamide, and the mixture is stirred at 80° C. for 2 h.

The solvent is then distilled off and the residue is taken up in 50 ml of water and adjusted to pH 2 using hydrochloric acid.

The precipitate is filtered off with suction.

Yield: 0.8 g (53% of theory), m.p.>250° C.

The following compounds of the formula (I-1-a) are obtained analogously to Example (I-1-a-1) and in accordance with the general statements on the preparation

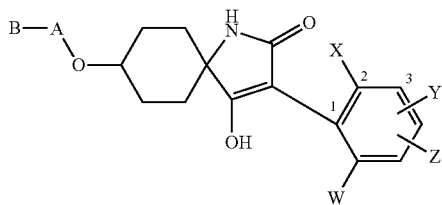

| Exp. No. | W | X | Y | Z | A | B | m.p. °C. | isomer |
|---|---|---|---|---|---|---|---|---|
| I-1-a-2 | CH$_3$ | CH$_3$ | 3-CH$_3$ | 4-CH$_3$ | —(CH$_2$)$_2$— | O-i-C$_3$H$_7$ | 195 | β |
| I-1-a-3 | CH$_3$ | CH$_3$ | 3-CH$_3$ | 4-CH$_3$ | —(CH$_2$)$_2$— | O—CH$_3$ | 224 | β |
| I-1-a-4 | CH$_3$ | CH$_3$ | H | 4-CH$_3$ | —(CH$_2$)$_2$— | O—CH$_3$ | 210 | β |
| I-1-a-5 | H | CH$_3$ | 5-CH$_3$ | H | —(CH$_2$)$_2$— | O—CH$_3$ | 102 | β |
| I-1-a-6 | CH$_3$ | CH$_3$ | 3-CH$_3$ | 4-CH$_3$ | —CH$_2$— | tetrahydrofuran-2-yl | 217 | β |
| I-1-a-7 | CH$_3$ | CH$_3$ | H | 4-CH$_3$ | —CH$_2$— | tetrahydrofuran-2-yl | 201 | β |
| I-1-a-8 | H | CH$_3$ | 5-CH$_3$ | 4-CH$_3$ | —CH$_2$— | tetrahydrofuran-2-yl | 118 | β |
| I-1-a-9 | H | CH$_3$ | 5-CH$_3$ | H | —CH$_2$— | tetrahydrofuran-2-yl | 103 | β |
| I-1-a-10 | CH$_3$ | CH$_3$ | H | 4-Cl | —CH$_2$— | tetrahydrofuran-2-yl | 208 | β |
| I-1-a-11 | CH$_3$ | CH$_3$ | H | 4-Cl | —CH$_2$— | H$_2$C=CH— | 224 | β |
| I-1-a-12 | CH$_3$ | Cl | H | 4-Cl | —CH$_2$— | H$_2$C=CH— | 204 | β |
| I-1-a-13 | CH$_3$ | Cl | H | 4-Cl | —CH$_2$— | H$_2$C=CH— | 196 | α* |
| I-1-a-14 | CH$_3$ | CH$_3$ | 3-CH$_3$ | 4-CH$_3$ | —CH$_2$— | C$_6$H$_5$— | 203 | β |
| I-1-a-15 | CH$_3$ | CH$_3$ | H | 4-CH$_3$ | —CH$_2$— | C$_6$H$_5$— | 78-80 | β |
| I-1-a-16 | H | CH$_3$ | 5-CH$_3$ | 4-CH$_3$ | —CH$_2$— | C$_6$H$_5$— | 81-83 | β |
| I-1-a-17 | H | CH$_3$ | 5-CH$_3$ | H | —CH$_2$— | C$_6$H$_5$— | 73-75 | β |
| I-1-a-18 | CH$_3$ | CH$_3$ | 5-CH$_3$ | 4-CH$_3$ | —CH$_2$— | 2-Cl—C$_6$H$_4$— | >240 | β |
| I-1-a-19 | CH$_3$ | CH$_3$ | H | 4-CH$_3$ | —CH$_2$— | 2-Cl—C$_6$H$_4$— | 202 | β |
| I-1-a-20 | H | CH$_3$ | 5-CH$_3$ | 4-CH$_3$ | —CH$_2$— | 2-Cl—C$_6$H$_4$— | 95 | β |
| I-1-a-21 | H | CH$_3$ | 5-CH$_3$ | H | —CH$_2$— | 2-Cl—C$_6$H$_4$— | 210 | β |
| I-1-a-22 | CH$_3$ | CH$_3$ | 3-CH$_3$ | 4-CH$_3$ | —CH$_2$— | 3-Cl—C$_6$H$_4$— | 228 | β |
| I-1-a-23 | CH$_3$ | CH$_3$ | H | 4-CH$_3$ | —CH$_2$— | 3-Cl—C$_6$H$_4$— | 125 | β |
| I-1-a-24 | H | CH$_3$ | 5-CH$_3$ | 4-CH$_3$ | —CH$_2$— | 3-Cl—C$_6$H$_4$— | 188 | β |
| I-1-a-25 | H | CH$_3$ | 5-CH$_3$ | H | —CH$_2$— | 3-Cl—C$_6$H$_4$— | 98 | β |
| I-1-a-26 | CH$_3$ | CH$_3$ | 3-CH$_3$ | 4-CH$_3$ | —CH$_2$— | 4-Cl—C$_6$H$_4$— | 130 | β |
| I-1-a-27 | CH$_3$ | CH$_3$ | H | 4-CH$_3$ | —CH$_2$— | 4-Cl—C$_6$H$_4$— | >250 | β |
| I-1-a-28 | H | CH$_3$ | 5-CH$_3$ | 4-CH$_3$ | —CH$_2$— | 4-Cl—C$_6$H$_4$— | >250 | β |
| I-1-a-29 | H | CH$_3$ | 5-CH$_3$ | H | —CH$_2$— | 4-Cl—C$_6$H$_4$— | >250 | β |
| I-1-a-30 | H | CH$_3$ | 5-(4-Cl—C$_6$H$_4$) | H | —CH$_2$— | 4-Cl—C$_6$H$_4$— | 158 | β |
| I-1-a-31 | H | Cl | 5-(4-Cl—C$_6$H$_4$) | H | —CH$_2$— | 4-Cl—C$_6$H$_4$— | 126 | β |
| I-1-a-32 | H | CH$_3$ | 5-CH$_3$ | H | —CH$_2$— | cyclohexyl | 173 | β |

*was obtained by chromatographic purification

Example I-1-b-1

Example I-1-c-1

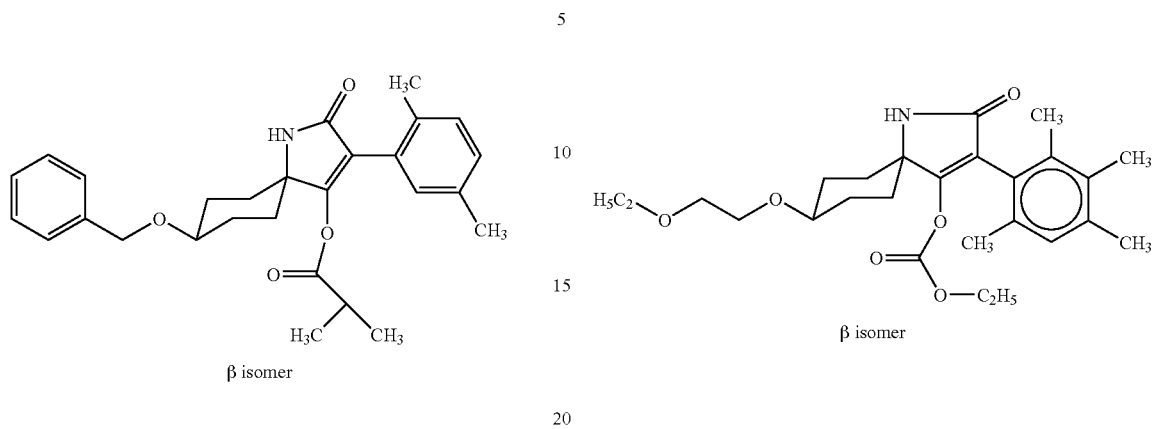

β isomer (left structure)

β isomer (right structure)

Under reflux, 0.63 ml (0.006 mol) of isobutyryl chloride in 5 ml of anhydrous ethyl acetate is added to 1.89 g (0.005 mol) of the compound of Preparation Example I-1-a-17 in 50 ml of anhydrous ethyl acetate and 0.84 ml (0.006 mol) of triethylamine.

The mixture is stirred under reflux and the reaction is monitored by thin-layer chromatography.

The reaction solution is concentrated using a rotary evaporator and the precipitate is taken up in dichloromethane and washed twice with 50 ml of 0.5N sodium hydroxide solution. Subsequently, the mixture is dried, the solvent is distilled off and the residue is recrystallized from methyl tert-butyl ether/n-hexane.

Yield: 1.07 g (46% of theory), m.p. 171° C.

The following compounds of the formula (I-1-b) are obtained analogously to Example (I-1-b-1) and in accordance with the general statements on the preparation 0.3 ml of triethylamine is added to 0.7 g (0.0018 mol) of the compound of Example I-1-a-1 in 30 ml of dichloromethane.

At 0° C., 0.2 g (0.0018 mol) of ethyl chloroformate in 5 ml of dichloromethane is added dropwise.

The mixture is stirred at room temperature for 1 day.

The solvent is removed using a rotary evaporatory and the residue is chromatographed on silica gel using the mobile phase dichloromethane/ethyl acetate 5:3.

Yield: 0.5 g (62.5% of theory), m.p. 101° C.

The following compounds of the formula (I-1-c) are obtained analogously to Example (I-1-c-1) and in accordance with the general statements on the preparation (I-1-b)

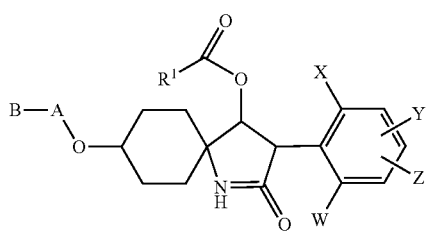

| Exp. No. | W | X | Y | Z | A | B | $R^1$ | m.p. °C. | isomer |
|---|---|---|---|---|---|---|---|---|---|
| I-1-b-2 | $CH_3$ | $CH_3$ | H | 4-$CH_3$ | —$CH_2$— | $C_6H_5$ | i-$C_3H_7$ | 195 | β |

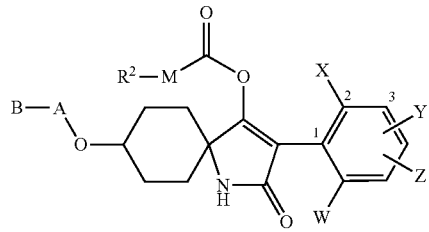

(I-1-c)

| Exp. No. | W | X | Y | Z | A | B | M | R² | m.p. °C. | isomer |
|---|---|---|---|---|---|---|---|---|---|---|
| I-1-c-2 | CH₃ | CH₃ | H | 4-Cl | —CH₂— | CH₂=CH— | O | C₂H₅ | 171 | β |
| I-1-c-3 | CH₃ | CH₃ | H | 4-CH₃ | —CH₂— | C₆H₅ | O | C₂H₅ | 164 | β |
| I-1-c-4 | H | CH₃ | 5-CH₃ | 4-CH₃ | —CH₂— | C₆H₅ | O | C₂H₅ | 131 | β |
| I-1-c-5 | H | CH₃ | 5-CH₃ | H | —CH₂— | C₆H₅ | O | C₂H₅ | 138 | β |

Example II-1

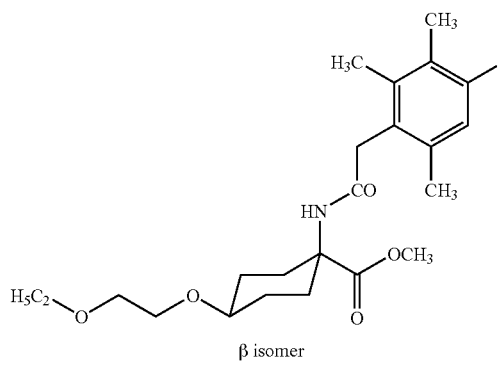

β isomer

At 0-10° C., 6 g of the compound of Preparation Example XIV-2 are initially charged in 100 ml of tetrahydrofuran and 2.8 ml of triethylamine. 4.5 g of 2,3,4,6-tetramethylphenylacetyl chloride in 30 ml of tetrahydrofuran and 2.8 ml of triethylamine in 30 ml of tetrahydrofuran are simultaneously added dropwise.

The mixture is stirred at 20° C. for one day.

The reaction mixture is filtered and the solvent is distilled off. The residue is chromatographed on silica gel using the mobile phase n-hexane:ethyl acetate 2:1.

Yield: 1.85 g (22.6% of theory), m.p. 108-110° C.

The following compounds of the formula (II) are obtained analogously to Example (II-1) and in accordance with the general statements on the preparation

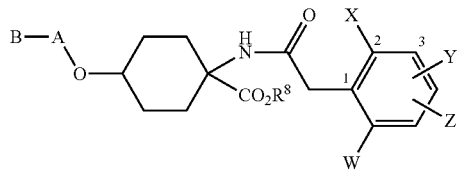

(II)

| Exp. No. | W | X | Y | Z | A | B | R⁸ | m.p. °C. | isomer |
|---|---|---|---|---|---|---|---|---|---|
| II-2 | CH₃ | CH₃ | 3-CH₃ | 4-CH₃ | —(CH₂)₂— | O-i-C₃H₇ | CH₃ | 133 | β |
| II-3 | CH₃ | CH₃ | 3-CH₃ | 4-CH₃ | —(CH₂)₂— | O—CH₃ | CH₃ | 104 | β |
| II-4 | CH₃ | CH₃ | H | 4-CH₃ | —(CH₂)₂— | O—CH₃ | CH₃ | 94 | β |
| II-5 | H | CH₃ | 5-CH₃ | H | —(CH₂)₂— | O—CH₃ | CH₃ | resin | β |
| II-6 | CH₃ | CH₃ | 3-CH₃ | 4-CH₃ | —CH₂— | tetrahydrofuran-2-yl | CH₃ | 126 | β |
| II-7 | CH₃ | CH₃ | H | 4-CH₃ | —CH₂— | tetrahydrofuran-2-yl | CH₃ | 111 | β |
| II-8 | H | CH₃ | 5-CH₃ | 4-CH₃ | —CH₂— | tetrahydrofuran-2-yl | CH₃ | 111 | β |

-continued

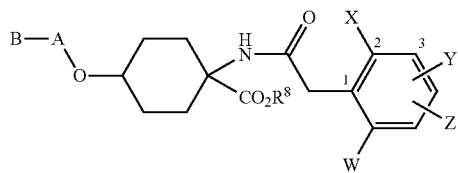

(II)

| Exp. No. | W | X | Y | Z | A | B | R⁸ | m.p. °C. | isomer |
|---|---|---|---|---|---|---|---|---|---|
| II-9 | H | $CH_3$ | 5-$CH_3$ | H | —$CH_2$— | (2-tetrahydrofuryl) | $CH_3$ | 101 | β |
| II-10 | $CH_3$ | $CH_3$ | H | 4-Cl | —$CH_2$— | (2-tetrahydrofuryl) | $CH_3$ | 139 | β |
| II-11 | $CH_3$ | $CH_3$ | H | 4-Cl | —$CH_2$— | $H_2C=CH—$ | $CH_3$ | 102 | β |
| II-12 | $CH_3$ | Cl | H | 4-Cl | —$CH_2$— | $H_2C=CH—$ | $CH_3$ | oil | β |
| II-13 | $CH_3$ | $CH_3$ | 3-$CH_3$ | 4-$CH_3$ | —$CH_2$— | $C_6H_5$ | $CH_3$ | 128-30 | β |
| II-14 | $CH_3$ | $CH_3$ | H | 4-$CH_3$ | —$CH_2$— | $C_6H_5$ | $CH_3$ | 112 | β |
| II-15 | H | $CH_3$ | 5-$CH_3$ | 4-$CH_3$ | —$CH_2$— | $C_6H_5$ | $CH_3$ | 111 | β |
| II-16 | H | $CH_3$ | 5-$CH_3$ | H | —$CH_2$— | $C_6H_5$ | $CH_3$ | 113 | β |
| II-17 | $CH_3$ | $CH_3$ | 5-$CH_3$ | 4-$CH_3$ | —$CH_2$— | 2-Cl—$C_6H_4$— | $CH_3$ | 154 | β |
| II-18 | $CH_3$ | $CH_3$ | H | 4-$CH_3$ | —$CH_2$— | 2-Cl—$C_6H_4$— | $CH_3$ | 131 | β |
| II-19 | H | $CH_3$ | 5-$CH_3$ | 4-$CH_3$ | —$CH_2$— | 2-Cl—$C_6H_4$— | $CH_3$ | 137 | β |
| II-20 | H | $CH_3$ | 5-$CH_3$ | H | —$CH_2$— | 2-Cl—$C_6H_4$— | $CH_3$ | 80 | β |
| II-21 | $CH_3$ | $CH_3$ | 3-$CH_3$ | 4-$CH_3$ | —$CH_2$— | 3-Cl—$C_6H_4$— | $CH_3$ | 131 | β |
| II-22 | $CH_3$ | $CH_3$ | H | 4-$CH_3$ | —$CH_2$— | 3-Cl—$C_6H_4$— | $CH_3$ | 111 | β |
| II-23 | H | $CH_3$ | 5-$CH_3$ | 4-$CH_3$ | —$CH_2$— | 3-Cl—$C_6H_4$— | $CH_3$ | 106 | β |
| II-24 | H | $CH_3$ | 5-$CH_3$ | H | —$CH_2$— | 3-Cl—$C_6H_4$— | $CH_3$ | 104 | β |
| II-25 | $CH_3$ | $CH_3$ | 3-$CH_3$ | 4-$CH_3$ | —$CH_2$— | 4-Cl—$C_6H_4$— | $CH_3$ | 115 | β |
| II-26 | $CH_3$ | $CH_3$ | H | 4-$CH_3$ | —$CH_2$— | 4-Cl—$C_6H_4$— | $CH_3$ | 113 | β |
| II-27 | H | $CH_3$ | 5-$CH_3$ | 4-$CH_3$ | —$CH_2$— | 4-Cl—$C_6H_4$— | $CH_3$ | 129 | β |
| II-28 | H | $CH_3$ | 5-$CH_3$ | H | —$CH_2$— | 4-Cl—$C_6H_4$— | $CH_3$ | 123 | β |
| II-29 | H | $CH_3$ | 5-(4-Cl—$C_6H_4$) | H | —$CH_2$— | 4-Cl—$C_6H_4$— | $CH_3$ | 132 | β |
| II-30 | H | Cl | 5-(4-Cl—$C_6H_4$) | H | —$CH_2$— | 4-Cl—$C_6H_4$— | $CH_3$ | 167 | β |
| II-31 | H | $CH_3$ | 5-$CH_3$ | H | —$CH_2$— | (cyclohexyl) | | 107 | β |
| II-32 | $CH_3$ | $CH_3$ | H | 4-$CH_3$ | —$CH_2$— | (cyclohexyl) | | 122 | β |

Example XIV-1

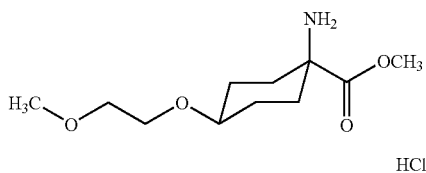

The crude product of Preparation Example XVII-1 is initially charged in 300 ml of anhydrous methanol. At 0-5° C., 20 ml of thionyl chloride are added dropwise and the mixture is stirred at 0° C. for 30 min. The mixture is then stirred at 40° C. overnight.

The reaction mixture is cooled, the potassium chloride is filtered off with suction and washed with methanol and the filtrate is concentrated to a volume of about 300 ml. More potassium chloride is filtered off with suction. The solvent is then distilled off completely and the residue is triturated with methyl tert-butyl ether. The precipitate is filtered off with suction.

Yield: 22 g (96% of theory) based on the amount of hydantoin used for preparing the compound of the formula XVII-1. The product still contains amounts of potassium chloride which were not quantified.

The following compounds of the formula (XIV) are obtained analogously to Example (XIV-1)

(XIV)

| Exp. No. | A | B | R | isomer | m.p. °C |
|---|---|---|---|---|---|
| XIV-2 | —(CH$_2$)— | H$_5$C$_2$—O— | CH$_3$ | β | 96 |
| XIV-3 | —(CH$_2$)— | i-C$_3$H$_7$— | CH$_3$ | β | 138 |
| XIV-4 | CH$_2$ | (tetrahydrofuranyl) | CH$_3$ | β | >250 |
| XIV-5 | CH$_2$ | CH$_2$=CH— | CH$_3$ | β | >250 |
| XIV-6 | CH$_2$ | C$_6$H$_5$ | CH$_3$ | β | 160 |
| XIV-7 | CH$_2$ | 2-Cl—C$_6$H$_4$ | CH$_3$ | β | 166 |
| XIV-8 | CH$_2$ | 3-Cl—C$_6$H$_4$ | CH$_3$ | | 168 |
| XIV-9 | CH$_2$ | 4-Cl—C$_6$H$_4$ | CH$_3$ | β | 184 |
| XIV 10 | CH$_2$ | (cyclohexyl) | CH$_3$ | β | decomp. |
| XIV-11 | CH$_2$ | (cyclopropyl) | CH$_3$ | β | decomp. |

Example XVII-1

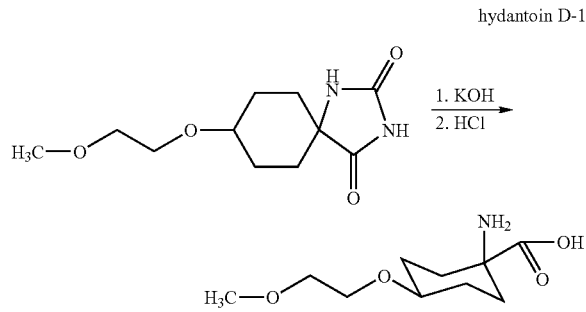

37 g of hydantoin D-1 are suspended in 0.51 in a 20% strength solution of potassium hydroxide. Under an atmosphere of inert gas, the mixture is boiled under reflux for 24 h.

The mixture is concentrated to about 25% of its original volume, acidified, at 0-10° C., with concentrated hydrochloric acid to pH 4-5, concentrated using a rotary evaporator and dried. The crude product is used directly for preparing the compound of Example XIV-1.

The following compounds of the formula (XVII) are obtained analogously to Example (XVII-1)

(XVII)

| Exp. No. | A | B | isomer |
|---|---|---|---|
| XVII-2 | —(CH$_2$)$_2$— | H$_5$C$_2$O— | β |
| XVII-3 | —(CH$_2$)$_2$— | i-C$_3$H$_7$O— | β |
| XVII-4 | —CH$_2$— | (tetrahydrofuranyl) | β |
| XVII-5 | —CH$_2$— | CH$_2$=CH— | β |
| XVII-6 | —CH$_2$— | C$_6$H$_5$ | β |
| XVII-7 | —CH$_2$— | 2-Cl—C$_6$H$_4$ | β |
| XVII-8 | —CH$_2$— | 3-Cl—C$_6$H$_4$ | β |
| XVII-9 | —CH$_2$— | 4-Cl—C$_6$H$_4$ | β |
| XVII-10 | —CH$_2$— | (cyclohexyl) | β |
| XVII-11 | —CH$_2$— | (cyclopropyl) | β |

The compounds of the formula (XVII) were used directly, without further purification steps, for preparing compounds of the formula (XIV).

General scheme for preparing the hydantoins (D) as products for preparing compounds of the formula (XVII)

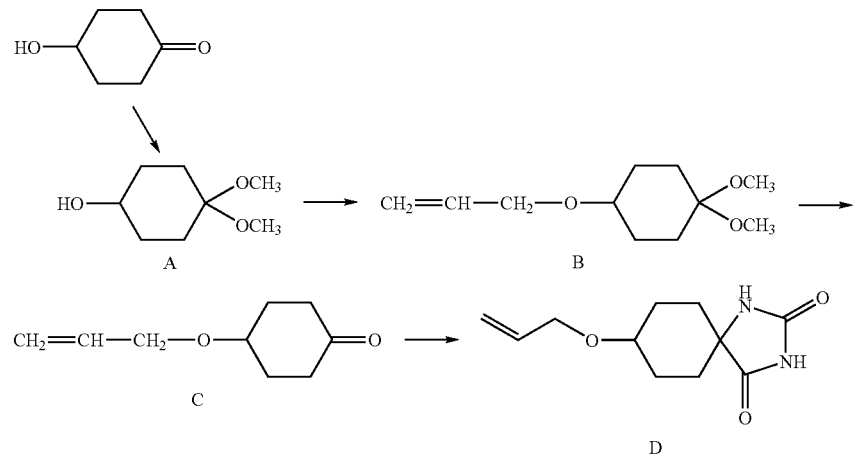

Preparation of Compound A

At room temperature, 260 g of methanol and 5 mg of para-toluenesulphonic acid in 20 ml of methanol are added to 94 g of 4-hydroxycyclohexanone in 275 ml of trimethyl orthoformate, and the mixture is boiled under reflux for 10 minutes. The mixture is then, at about 0° C., neutralized with aqueous sodium bicarbonate solution and concentrated. The residue is chromatographed on silica gel using the mobile phase hexane/acetone 7/3.

Yield: 125 g (95% of theory).

Preparation of Compound B

At room temperature, 150 g of potassium tert-butoxide and 151 g of allyl bromide are added to 200 g of compound A in 1500 ml of tert-butanol, and the mixture is stirred at about 60° C. for one day. The mixture is then diluted with water and extracted with methylene chloride, and the organic phase is concentrated. The residue is chromatographed on silica gel using the mobile phase hexane/acetone 10/1.

Yield: 215 g (86% of theory).

Preparation of Compound C 233 g of compound B in 1000 ml of tetrahydrofuran (THF) and 750 ml of 1N HCl are stirred at room temperature for 2 hours. Water is then added, and the mixture is extracted with methylene chloride. The organic phase is concentrated.

Yield: 157 g (88% of theory).

Preparation of Compound D 370 g (3.86 mol) of ammonium carbonate are initially charged in 670 ml of water. 82 g (1.67 mol) of sodium cyanide and 130 g (0.83 mol) of compound C in 760 ml of ethanol are added. The mixture is stirred at 55-60° C. for 10 hours and at room temperature overnight. The reaction solution is then, at 0-5° C., adjusted to pH 1-2 using about 575 ml of concentrated hydrochloric acid. The mixture is flushed with nitrogen and stirred at 0-5° C. for 1 hour. The precipitate is filtered off with suction in the cold and not washed.

Yield: 219.5 g (100% of theory), m.p. 184-192° C., contaminated with carbonate salts.

Example A

Meloidogyne Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita egg/larvae suspension and lettuce seeds. The lettuce seeds germinate and the plants develop. On the roots, galls are formed.

After the desired period of time, the nematicidal action is determined in % by the gall formation. 100% means that no galls have been found; 0% means that the number of galls on the treated plants corresponds to that of the untreated control.

In this test, for example, the following compounds of the Preparation Examples show good activity:

TABLE A

Plant-damaging nematodes *Meloidogyne* test

| Active compounds | Concentration of active compound in ppm | Effect in % after 14$^d$ |
|---|---|---|
| Ex. I-1-a-22 | 20 | 98 |
| Ex. I-1-a-26 | 20 | 100 |
| Ex. I-1-c-2 | 20 | 100 |
| Ex. I-1-a-31 | 20 | 95 |

Example B

Myzus Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) which are heavily infested by the peach aphid (Myzus persicae) are treated by being dipped into the preparation of active compound of the desired concentration.

After the desired period of time, the kill in % is determined 100% means that all aphids have been killed; 0% means that none of the aphids have been killed.

In this test, for example, the following compounds of the Preparation Examples show good activity:

TABLE B

Plant-damaging insects *Myzus* test

| Active compounds | Concentration of active compound in ppm | Kill rate in % after 6$^d$ |
|---|---|---|
| Ex. I-1-a-2 | 1000 | 100 |
| Ex. I-1-a-4 | 1000 | 90 |
| Ex. I-1-a-5 | 1000 | 98 |
| Ex. I-1-c-2 | 500 | 95 |
| Ex. I-1-a-30 | 500 | 100 |

Example C

Phaedon Larvae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with larvae of the mustard beetle (Phaedon cochleariae) while the leaves are still moist.

After the desired period of time, the kill in % is determined 100% means that all beetle larvae have been killed; 0% means that none of the beetle larvae have been killed.

In this test, for example, the following compounds of the Preparation Examples show good activity:

TABLE C

Plant-damaging insects Phaedon larvae test

| Active compounds | Concentration of active compound in ppm | Kill rate in % after $7^d$ |
|---|---|---|
| Ex. I-1-a-2 | 1000 | 100 |
| Ex. I-1-a-21 | 1000 | 100 |
| Ex. I-1-a-25 | 1000 | 100 |
| Ex. I-1-a-20 | 1000 | 100 |
| Ex. I-1-a-22 | 1000 | 100 |
| Ex. I-1-a-26 | 1000 | 100 |
| Ex. I-1-a-10 | 1000 | 100 |
| Ex. I-1-a-6 | 1000 | 100 |
| Ex. I-1-a-9 | 1000 | 100 |
| Ex. I-1-a-7 | 1000 | 100 |
| Ex. I-1a-3 | 1000 | 100 |

Example D

Spodoptera Frugiperda Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with caterpillars of the army worm (Spodoptera frugiperda) while the leaves are still moist.

After the desired period of time, the kill in % is determined 100% means that all caterpillars have been killed; 0% means that none of the caterpillars have been killed.

In this test, for example, the following compounds of the Preparation Examples show good activity:

TABLE D

Plant-damaging insects Spodoptera frugiperda test

| Active compounds | Concentration of active compound in ppm | Kill rate in % after $7^d$ |
|---|---|---|
| Ex. I-1-a-4 | 1000 | 100 |
| Ex. I-1-a-5 | 1000 | 100 |
| Ex. I-1-a-8 | 1000 | 100 |
| Ex. I-1-a-11 | 500 | 100 |
| Ex. I-1-a-12 | 500 | 100 |
| Ex. I-1-a-31 | 500 | 100 |

Example E

Spodoptera Frugiperda Test/Synthetic Feed

Solvent: 31 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

A stated amount of the preparation of active compound of the desired concentration is pipetted onto a standardized amount of synthetic feed. In 6 replications, in each case one larva (L3) of the army worm (Spodoptera frugiperda) is placed onto the feed.

After the desired period of time, the kill in % is determined 100% means that all animals have been killed; 0% means that none of the animals have been killed.

In this test, for example, the following compound of the Preparation Examples shows good activity:

TABLE E

Plant-damaging insects Spodoptera frugiperda test/synthetic feed

| Active compound | Concentration of active compound in ppm | Kill rate in % after $7^d$ |
|---|---|---|
| Ex. I-1-b-1 | 1000 | 100 |

Example F

Tetranychus Test (OP-Resistant/Dip Treatment)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (Phaseolus vulgaris) which are heavily infested by all stages of the greenhouse red spider mite (Tetranychus urticae) are dipped into a preparation of active compound of the desired concentration.

After the desired period of time, the effect in % is determined 100% means that all spider mites have been killed; 0% means that none of the spider mites have been killed.

In this test, for example, the following compounds of the Preparation Examples show good activity:

TABLE F

Plant-damaging mites Tetranychus test (OP-resistant/dip treatment)

| Active compounds | Concentration of active compound in ppm | Kill rate in % after $7^d$ |
|---|---|---|
| Ex. I-1-a-2 | 100 | 95 |
| Ex. I-1-a-3 | 100 | 98 |
| Ex. I-1-a-11 | 100 | 95 |
| Ex. I-1-a-31 | 100 | 99 |
| Ex. I-1-a-30 | 100 | 99 |

Example G

Botrytis Test (Bean)/Protective

Solvents: 24.5 parts by weight of acetone
24.5 parts by weight of dimethylacetamide
Emulsifier: 1.0 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, 2 small pieces of agar colonized by Botrytis cinerea are placed onto each leaf. The inoculated plants are placed in a dark chamber at about 20° C. and 100% relative atmospheric humidity.

2 days after the inoculation, the size of the infested areas of the leaves is evaluated. 0% means an efficacy which corresponds to that of the control, whereas an efficacy of 100% means that no infection is observed.

TABLE G

Botrytis test (bean)/protective

| Active compounds | Active compound application rate in g/ha | % efficacy |
|---|---|---|
| Ex. I-1-a-30 | 500 | 100 |

Example H

Post-Emergence Test

Solvent: 5 parts by weight of acetone
Emulsifier: 1 part by weight of alkyaryl polyglycol ether
To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction Example I Pre-Emergence Test Solvent: 5 parts by weight of acetone
Emulsifier: 1 part by weight of alkyaryl polyglycol ether
To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction

| post-emergence | g of ai/ha | Sugar beet | Alopecurus | Cyperus | Setaria | Sinapis |
|---|---|---|---|---|---|---|
| Ex. I-1-b-2 | 250 | 0 | 80 | 80 | 95 | 70 |

| pre-emergence | g of ai/ha | Alopecurus | Avena fatua | Setaria | Sinapis |
|---|---|---|---|---|---|
| Ex. I-1-c-3 | 125 | 90 | 70 | 100 | 90 |

| pre-emergence | g of ai/ha | Maize | Digitaria | Eriochloa | Lolium | Setaria | Ipomoea |
|---|---|---|---|---|---|---|---|
| Ex. I-1-a-23 | 125 | 0 | 100 | 99 | 80 | 95 | 80 |

| post-emergence | g of ai/ha | Sugar beet | Avena fatua | Setaria | Abutilon | Amaranthus | Sinapis |
|---|---|---|---|---|---|---|---|
| Ex. I-1-a-23 | 250 | 0 | 80 | 95 | 80 | 90 | 90 |

| post-emergence | g of ai/ha | Alopecurus | Abutilon | Amaranthus | Galium | Sinapis |
|---|---|---|---|---|---|---|
| Ex. I-1-a-27 | 250 | 90 | 80 | 90 | 70 | 80 |

| post-emergence | g of ai/ha | Sugar beet | Alopecurus | Setaria | Amaranthus | Sinapis |
|---|---|---|---|---|---|---|
| Ex. I-1-a-10 | 250 | 0 | 70 | 95 | 90 | 80 |

| pre-emergence | g of ai/ha | Sugar beet | Echinochloa | Setaria | Sinapis |
|---|---|---|---|---|---|
| Ex. I-1-a-7 | 250 | 0 | 99 | 100 | 90 |

| pre-emergence | g of ai/ha | Alopecurus | Echinochloa | Setaria | Sinapis |
|---|---|---|---|---|---|
| Ex. I-1-a-13 | 2000 | 95 | 95 | 100 | 70 |

| pre-emergence | g of ai/ha | Alopecurus | Avena fatua | Echinochloa | Setaria | Amaranthus | Sinapis |
|---|---|---|---|---|---|---|---|
| Ex. I-1-a-4 | 250 | — | 100 | 100 | 100 | 95 | 99 |
| Ex. I-1-a-11 | 2000 | 100 | 100 | 100 | 100 | 95 | 90 |
| Ex. I-1-a-12 | 2000 | 100 | 80 | 100 | 100 | 90 | 80 |

| post-emergence | g of ai/ha | Alopecurus | Avena fatua | Setaria | Abutilon | Amaranthus | Sinapis |
|---|---|---|---|---|---|---|---|
| Ex. I-1-a-4 | 250 | 80 | 95 | 99 | — | 95 | 80 |
| Ex. I-1-a-7 | 250 | 80 | 95 | 99 | — | 95 | 90 |
| Ex. I-1-a-11 | 2000 | 95 | 70 | 100 | 90 | 80 | — |
| Ex. I-1-a-12 | 2000 | 95 | 95 | 95 | 80 | — | 90 |
| Ex. I-1-a-13 | 2000 | 90 | — | 80 | 80 | — | 80 |

Example J

Critical Concentration Test/Soil Insects

Treatment of Transgenic Plants

Test insect: Diabrotica balteata—larvae in soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. The concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example K

Heliothis Virescens Test

Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (Glycine max) of the cultivar Roundup Ready (trade mark of Monsanto Comp., USA) are treated by being dipped into the preparation of active compound of the desired concentration and are populated with the tobacco bud worm caterpillar Heliothis virescens while the leaves are still moist.

After the desired period of time, the kill of the insects is determined.

The invention claimed is:

1. A compound of formula (XVII),

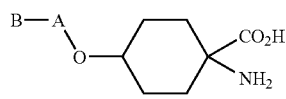

(XVII)

in which
A represents an optionally substituted alkanediyl group; and
B represents optionally halogen substituted alkenyl, alkoxy, or alkoxyalkyloxy, or represents substituted phenyl; or represents cycloalkyl that is optionally substituted and/or in which the cycloalkyl ring is optionally interrupted by one or more heteroatoms and/or C=O.

2. A compound according to claim 1 in which
A represents an optionally $C_1$-$C_4$-alkyl-substituted $C_1$-$C_4$-alkanediyl group; and
B represents optionally halogen-substituted $C_2$-$C_8$-alkenyl, $C_1$-$C_6$-alkoxy, or $C_1$-$C_6$-alkoxy-$C_1$-$C_4$-alkyloxy; represents halogen-, $C_1$-$C_6$-alkyl-, $C_1$-$C_6$-alkoxy-, $C_1$-$C_4$-haloalkyl-, $C_1$-$C_4$-haloalkoxy-, cyano-, or nitro-substituted phenyl; or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which one or two methylene groups of the cycloalkyl ring that are not directly adjacent are optionally replaced by oxygen or three methylene groups of the cycloalkyl ring are optionally replaced by a group —O—CO—O—.

3. A compound of formula (XIV)

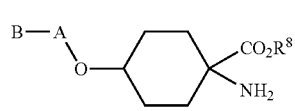

(XIV)

in which
A represents an optionally substituted alkanediyl group;
B represents optionally halogen substituted alkenyl, alkoxy, or alkoxyalkyloxy, or represents substituted phenyl; or represents cycloalkyl that is optionally substituted and/or in which the cycloalkyl ring is optionally interrupted by one or more heteroatoms and/or C=O, and
$R^8$ represents alkyl.

4. A compound according to claim 3 in which
A represents an optionally $C_1$-$C_4$-alkyl-substituted $C_1$-$C_4$-alkanediyl group;
B represents optionally halogen-substituted $C_2$-$C_8$-alkenyl, $C_1$-$C_6$-alkoxy, or $C_1$-$C_6$-alkoxy-$C_1$-$C_4$-alkyloxy; represents halogen-, $C_1$-$C_6$-alkyl-, $C_1$-$C_6$-alkoxy-, $C_1$-$C_4$-haloalkyl-, $C_1$-$C_4$-haloalkoxy-, cyano-, or nitro-substituted phenyl; or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which one or two methylene groups of the cycloalkyl ring that are not directly adjacent are optionally replaced by oxygen or three methylene groups of the cycloalkyl ring are optionally replaced by a group —O—CO—O—, and
$R^8$ represents $C_1$-$C_6$-alkyl.

* * * * *